(12) United States Patent
Makifuchi

(10) Patent No.: US 9,672,949 B2
(45) Date of Patent: Jun. 6, 2017

(54) X-RAY IMAGING SYSTEM AND IMAGE PROCESSING METHOD

(71) Applicant: Konica Minolta, Inc., Chiyoda-ku, Tokyo (JP)

(72) Inventor: Chiho Makifuchi, Hino (JP)

(73) Assignee: KONICA MINOLTA, INC., Chiyoda-Ku, Tokyo (JP)

( * ) Notice: Subject to any disclaimer, the term of this patent is extended or adjusted under 35 U.S.C. 154(b) by 103 days.

(21) Appl. No.: 14/596,615

(22) Filed: Jan. 14, 2015

(65) Prior Publication Data

US 2015/0235725 A1    Aug. 20, 2015

(30) Foreign Application Priority Data

Feb. 14, 2014 (JP) ................................ 2014-026087

(51) Int. Cl.
| | |
|---|---|
| *A61B 6/04* | (2006.01) |
| *G21K 1/06* | (2006.01) |
| *G06T 5/00* | (2006.01) |
| *A61B 6/00* | (2006.01) |
| *G01N 23/201* | (2006.01) |
| *G01N 23/04* | (2006.01) |

(52) U.S. Cl.
CPC ............ *G21K 1/067* (2013.01); *A61B 6/4233* (2013.01); *A61B 6/4291* (2013.01); *A61B 6/484* (2013.01); *A61B 6/5205* (2013.01); *A61B 6/5258* (2013.01); *A61B 6/586* (2013.01); *G06T 5/002* (2013.01); *G01N 23/04* (2013.01); *G01N 23/201* (2013.01); *G01N 2223/045* (2013.01); *G06T 2207/10116* (2013.01); *G06T 2207/30008* (2013.01)

(58) Field of Classification Search
CPC combination set(s) only.
See application file for complete search history.

(56) References Cited

U.S. PATENT DOCUMENTS

| | | | | |
|---|---|---|---|---|
| 8,989,474 | B2* | 3/2015 | Kido ..................... | A61B 6/4291 382/132 |
| 9,025,725 | B2* | 5/2015 | Kiyohara ................. | A61B 6/06 378/197 |
| 2004/0071363 | A1* | 4/2004 | Kouri ................. | G06K 9/00516 382/276 |
| 2014/0198895 | A1* | 7/2014 | Hoshino ................ | A61B 6/482 378/36 |
| 2016/0022235 | A1* | 1/2016 | Ning ...................... | A61B 6/032 378/4 |

FOREIGN PATENT DOCUMENTS

JP    2011223545 A1    11/2011

\* cited by examiner

*Primary Examiner* — Phillip A Johnston
*Assistant Examiner* — Hsien Tsai
(74) *Attorney, Agent, or Firm* — Cantor Colburn LLP

(57) ABSTRACT

The X-ray imaging system of this invention includes: a detecting member which detects a salt and pepper noise region in the reconstructed image based on at least one characteristic value of the moire stripe image not including the object and/or the moire stripe image including the object; a masked-image generating member which generates a masked image for identifying the detected salt and pepper noise region; and an image processing member which masks or trims at least one of the reconstructed image and the moire stripe images with the generated masked image.

5 Claims, 19 Drawing Sheets

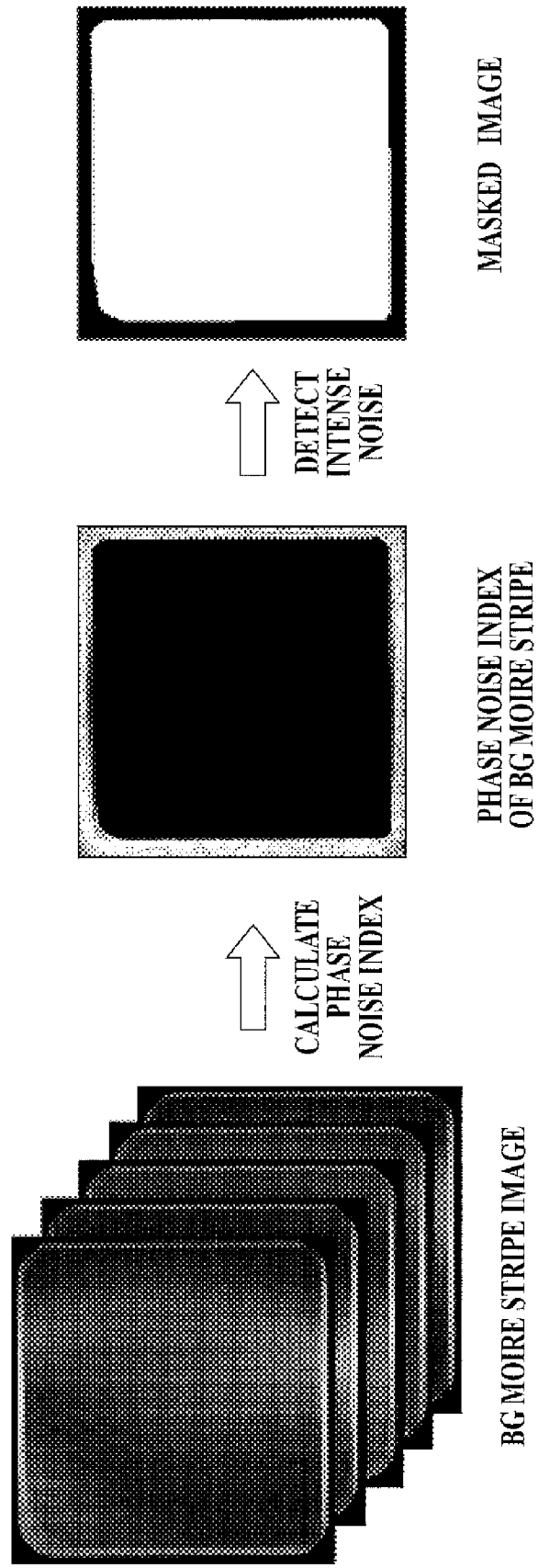

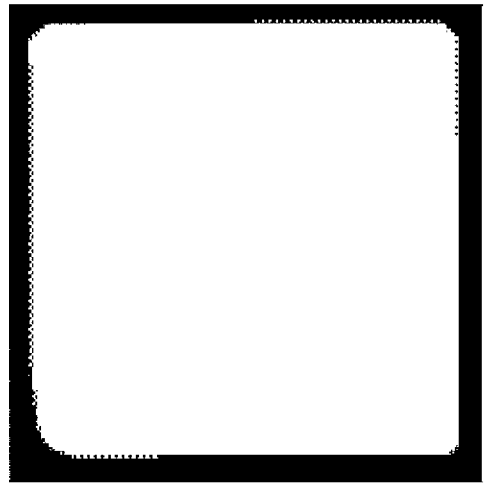
FIG.14C DETECTION BY AMPLITUDE
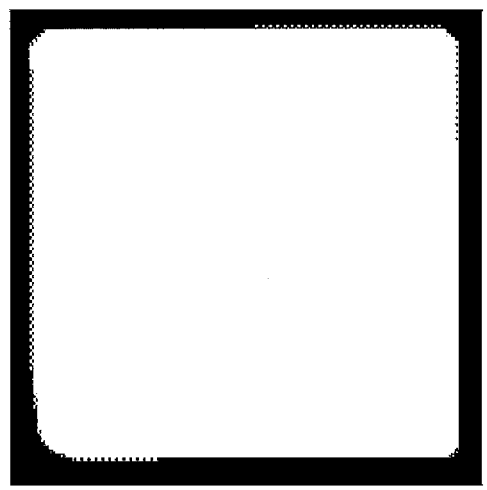
FIG.14B DETECTION BY DEFINITION ERROR
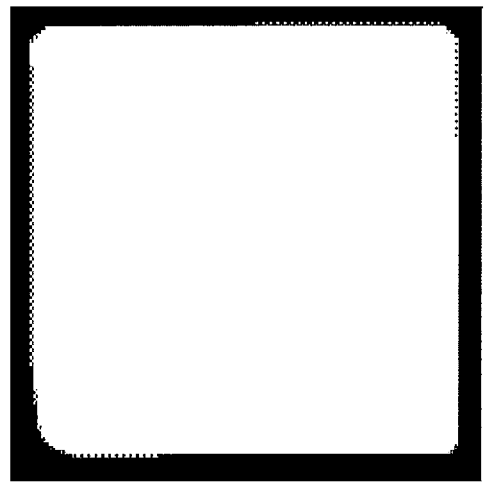
FIG.14A DETECTION BY PHASE ERROR

FIG.15
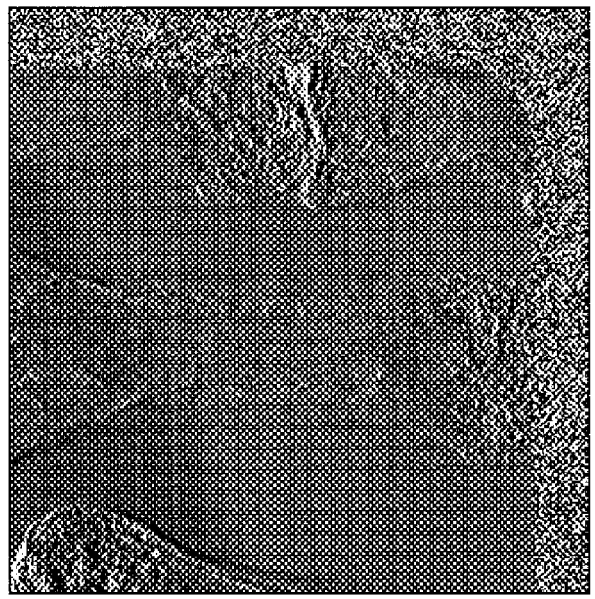
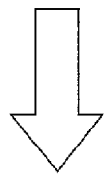
MASKING
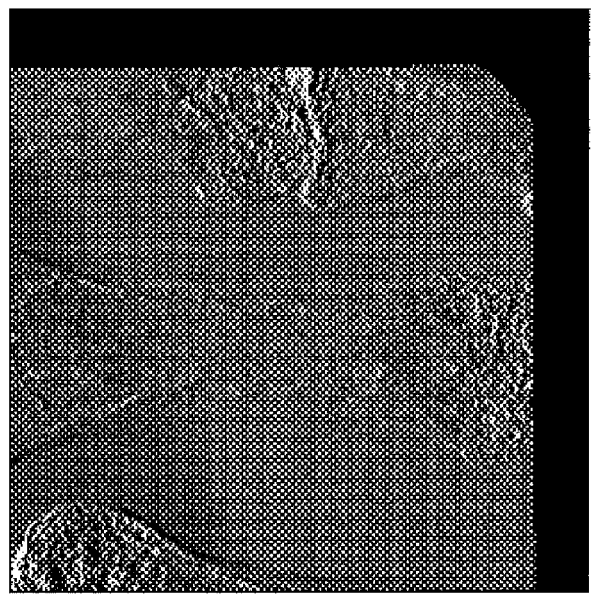

FIG.16
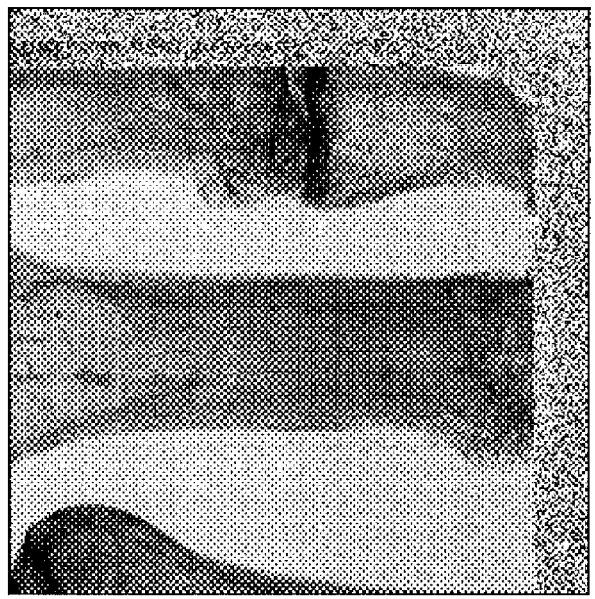
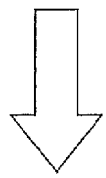
MASKING

FIG.17
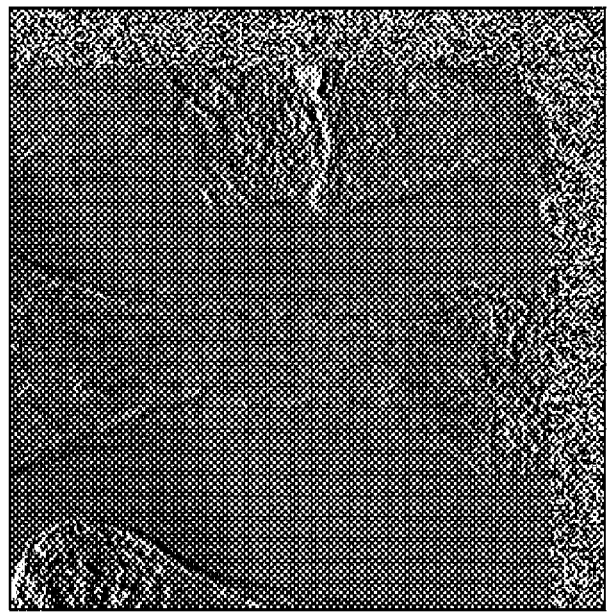
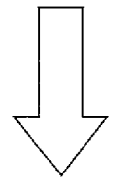
TRIMMING
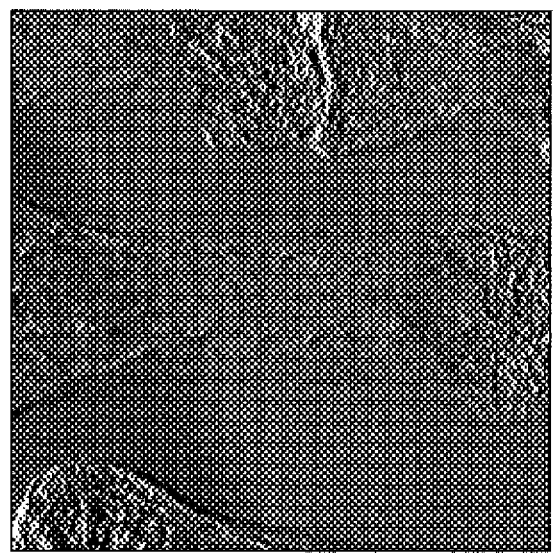

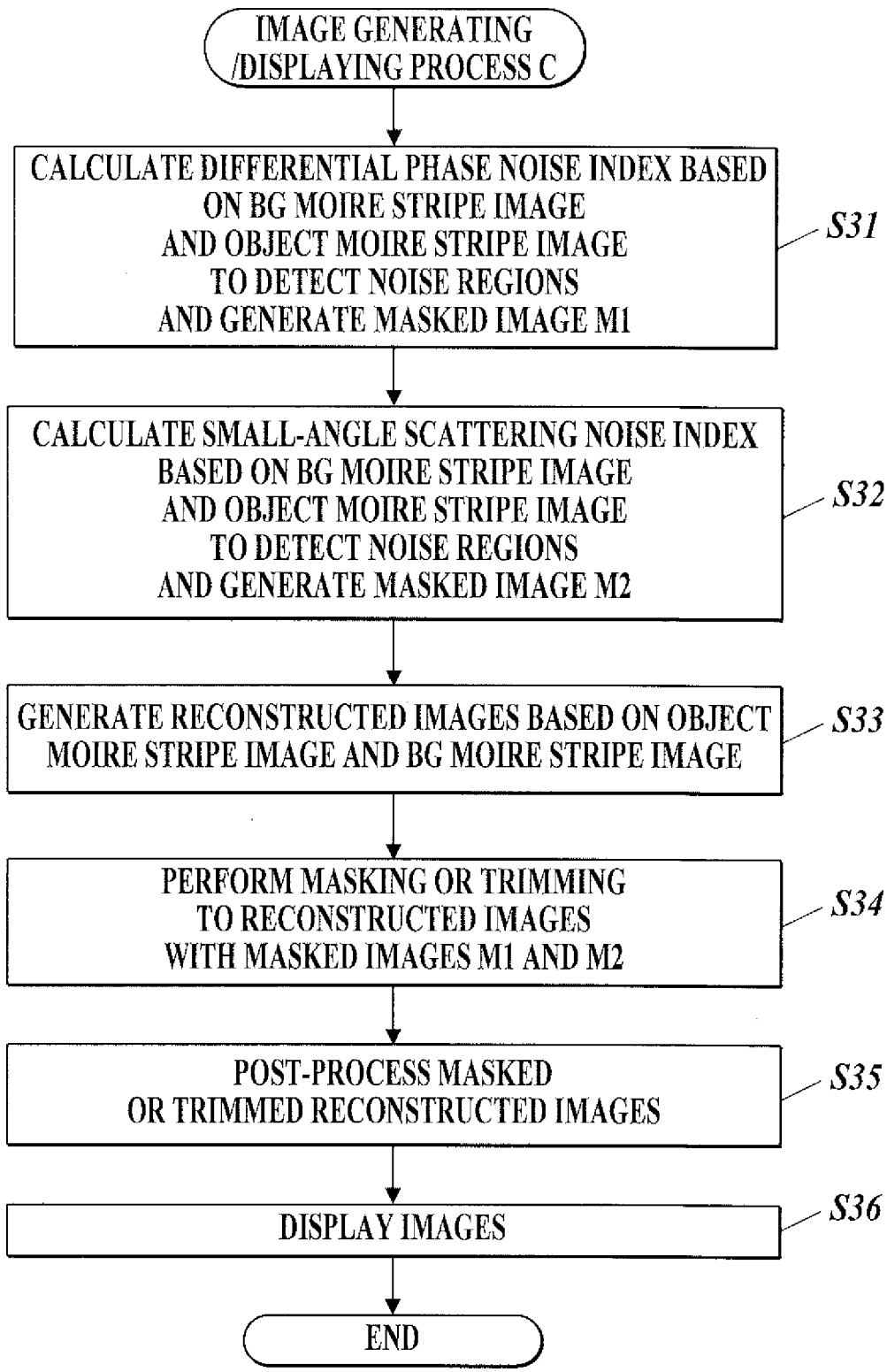

*FIG.21C*  ABSORPTION IMAGE
*FIG.21B*  SMALL-ANGLE SCATTERING IMAGE
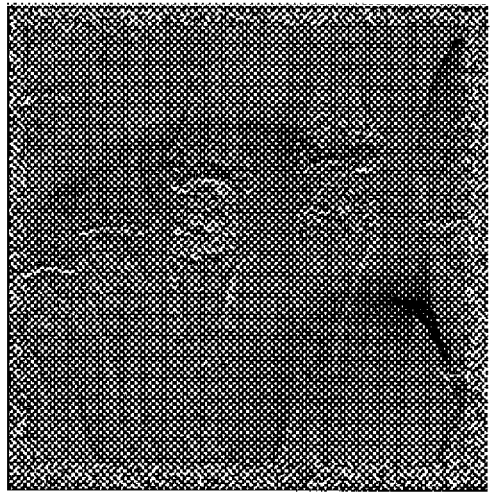
*FIG.21A*  DIFFERENTIAL PHASE IMAGE

X-RAY IMAGING SYSTEM AND IMAGE PROCESSING METHOD

CROSS REFERENCE TO RELATED APPLICATION

The present invention claims priority under 35 U.S.C. §119 to Japanese Application No. 2014-026087 filed Feb. 14, 2014, the entire content of which is incorporated herein by reference.

BACKGROUND OF THE INVENTION

Field of the Invention

The present invention relates to an X-ray imaging system and an image processing method.

Description of Related Art

Radiographic imaging systems for X-ray phase imaging are known that include gratings disposed between radiation sources and radiation detectors. Techniques are also known that detect defects in pixels caused by deformed gratings in such radiographic imaging systems (for example, refer to Patent document 1 (Japanese Patent No. 5378335)).

Conventional absorption images include regions unsuitable for imaging, such as regions outside the radiation field (low-intensity X-ray regions), where an amount of X-rays to reach the radiation detector is insufficient and thereby object signals are absent (see FIG. 21C). Such low-intensity X-ray regions are detected through radiation-field recognition of the absorption images and are usually masked.

Differential phase images and small-angle scattering images acquired through phase-contrast imaging with gratings are unsatisfactory for imaging because object signals are absent due to a lack of a moire stripe pattern not only in the low-intensity X-ray regions but also in the out-of-grating regions through which incident X-rays do not pass through grating structure portions of all gratings. In such region, photon errors and detector errors are amplified through computation, causing a large variation in the signal values that generates "salt and pepper noise" (see FIGS. 21A and 21B). Because of containing out-of-grating regions, such regions of salt and pepper noise cannot be correctly recognized through conventional methods based only on X-ray intensity, such as radiation-field recognition. Salt and pepper noise significantly impairs the image quality. Moreover, the time required for diagnosis and examination by medical doctors increases because the doctors must visually distinguish between regions of salt and pepper noise and regions corresponding to the object, and this increases the work burden applied to the operator. The salt and pepper noise contained in reconstructed images (differential phase images, small-angle scattering images, and absorption images) significantly impairs the stability of image processing (post-processing) performed on the images, such as correction and combination, and computation for unnecessary regions increases the processing time.

The radiographic imaging system according to Patent document 1 detects manufacturing defects in pixel units in the in-grating regions and defects in the detector and corrects these defects with peripheral pixels. The regions outside the X-ray irradiation field and the out-of-grating regions remain uncorrected.

SUMMARY OF THE INVENTION

An object of the present invention is to provide readily diagnosable and examinable differential phase images and small-angle scattering images and to enhance the stability and speed of post-processing carried out on these images.

To solve the above problems, an X-ray imaging system, to which one aspect of the present invention is reflected, includes: an X-ray source which emits an X-ray; a first grating having a periodic pattern and disposed in an X-ray propagating path; a second grating which converts the periodic pattern of the first grating into a moire stripe pattern; an X-ray detector including two-dimensionally arrayed transducers which generate an electrical signal corresponding to the incident X-ray emitted from the X-ray source and passing through the first grating and the second grating, the X-ray detector reading the electrical signal generated by the transducers as an image signal to acquire a moire stripe image; a reconstructed image generating member which generates at least one reconstructed image of a differential phase image and a small-angle scattering image of an object based on a moire stripe image not including the object and a moire stripe image including the object, the moire stripe image not including the object being acquired through irradiation of an object position without the object in the X-ray propagating path with the X-ray from the X-ray source, the moire stripe image including the object being acquired through irradiation of the object at the object position with the X-ray from the X-ray source; a detecting member which detects a salt and pepper noise region in the reconstructed image based on at least one characteristic value of the moire stripe image not including the object and/or the moire stripe image including the object; a masked-image generating member which generates a masked image for identifying the detected salt and pepper noise region; and an image processing member which masks or trims at least one of the reconstructed image and the moire stripe images with the generated masked image.

The method of processing an image in an X-ray imaging system, to which method one aspect of the present invention is reflected, the system including: an X-ray source which emits an X-ray; a first grating having a periodic pattern and disposed in an X-ray propagating path; a second grating which converts the periodic pattern of the first grating into a moire stripe pattern; an X-ray detector including two-dimensionally arrayed transducers which generate an electrical signal corresponding to the incident X-ray emitted from the X-ray source and passing through the first grating and the second grating, the X-ray detector reading the electrical signal generated by the transducers as an image signal to acquire a moire stripe image; and a reconstructed image generating member which generates at least one reconstructed image of a differential phase image and a small-angle scattering image of an object based on a moire stripe image not including the object and a moire stripe image including the object, the moire stripe image not including the object being acquired through irradiation of an object position without the object in the X-ray propagating path with the X-ray from the X-ray source, the moire stripe image including the object being acquired through irradiation of the object at the object position with the X-ray from the X-ray source, and the method including the steps of: detecting a salt and pepper noise region in the reconstructed image based on at least one characteristic value of the moire stripe image not including the object and/or the moire stripe image including the object; generating a masked image for identifying the detected salt and pepper noise region; and masking or trimming at least one of the reconstructed image and the moire stripe images with the generated masked image.

The present invention can provide readily diagnosable and examinable differential phase images and small-angle scattering images. The present invention can also enhance the stability and speed of post-processing carried out on these images.

BRIEF DESCRIPTION OF THE DRAWINGS

The present invention will become more fully understood from the detailed description given hereinbelow and the appended drawings, and thus are not intended as a definition of the limits of the present invention, and wherein:

FIG. 11 illustrates the generating process of a masked image with a phase noise index of BG moire stripe images.

FIG. 14A illustrates a masked image generated based on the detected noise due to a phase error.

FIG. 14B illustrates a masked image generated based on the detected noise due to a visibility error.

FIG. 14C illustrates a masked image generated based on the detected noise due to amplitude.

FIG. 15 illustrates the result of an example masking process of a differential phase image.

FIG. 16 illustrates the result of an example masking process of a small-angle scattering image.

FIG. 17 illustrates the result of an example trimming process of a differential phase image.

FIG. 19 is a flowchart illustrating an image generating/displaying process C performed by the control unit in FIG. 4 according to a third embodiment.

FIG. 21A illustrates an example differential phase image.

FIG. 21B illustrates an example small-angle scattering image.

FIG. 21C illustrates an example absorption image.

PREFERRED EMBODIMENT OF THE PRESENT INVENTION

<First Embodiment>

A first embodiment of the present invention will now be described with reference to the accompanying drawings.

Figure 1:
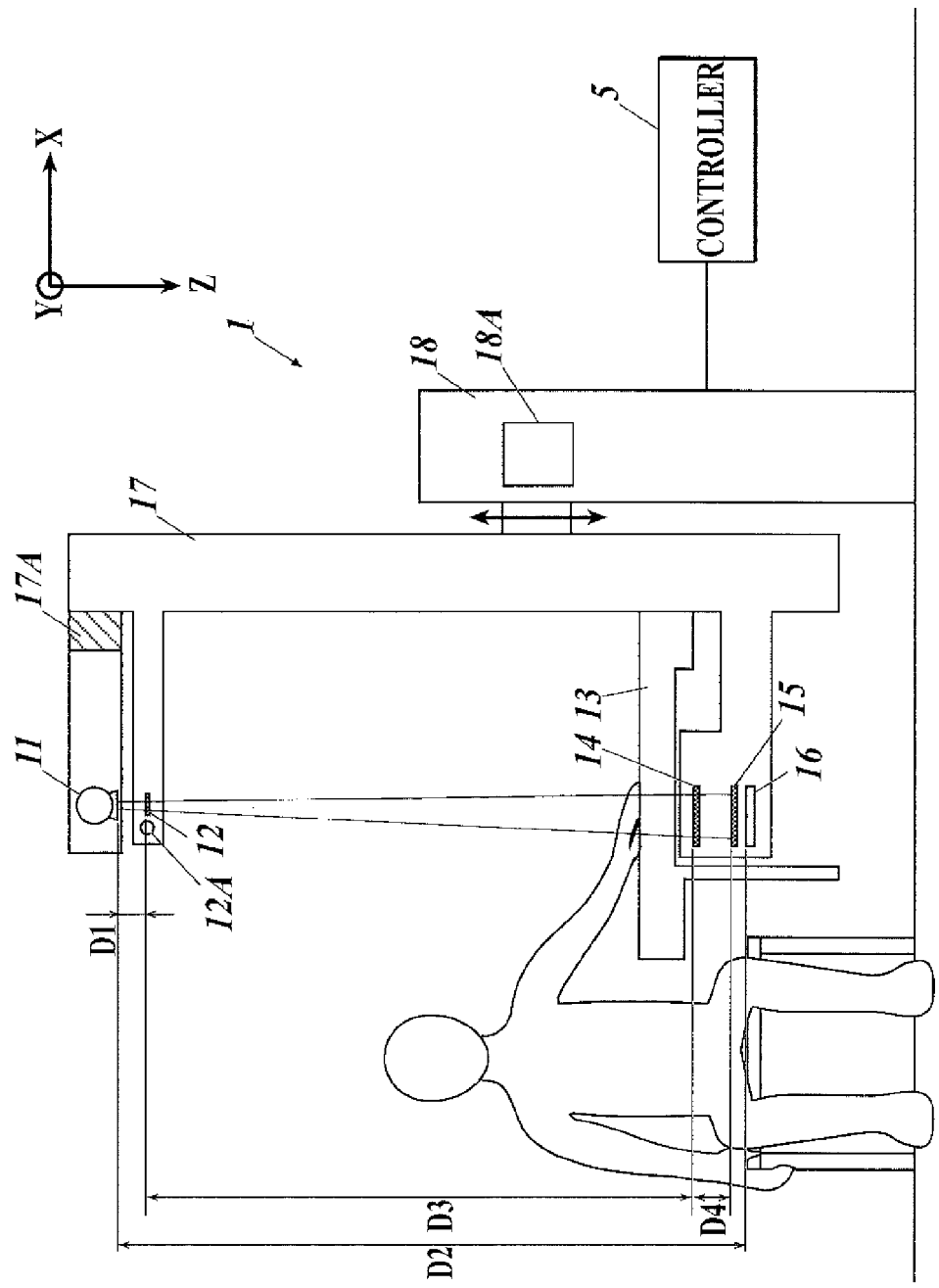
FIG. 1 illustrates the overall configuration of an X-ray imaging system according to an embodiment.

FIG. 1 illustrates an X-ray imaging system according to the first embodiment. The X-ray imaging system includes an X-ray imaging apparatus 1 and a controller 5. The X-ray imaging apparatus 1 performs X-ray imaging with a Talbot-Lau interferometer. The controller 5 generates a reconstructed image of an object from a plurality of moire stripe images acquired through the X-ray imaging.

With reference to FIG. 1, the X-ray imaging apparatus 1 includes an X-ray source 11, a multislit grating 12, an object table 13, a first grating 14, a second grating 15, an X-ray detector 16, a support unit 17, and a main unit 18.

The X-ray imaging apparatus 1 is of an up-right type in which the X-ray source 11, the multislit grating 12, the object table 13, the first grating 14, the second grating 15, and the X-ray detector 16 are disposed along the Z or gravity direction. The distance between the focus of the X-ray source 11 and the multislit grating 12 is D1 (mm); the distance between the focus of the X-ray source 11 and the X-ray detector 16 is D2 (mm); the distance between the multislit grating 12 and the first grating 14 is D3 (mm); and the distance between the first grating 14 and the second grating 15 is D4 (mm). The object table 13 may be disposed between the first grating 14 and the second grating 15.

The distance D1 is preferably 5 to 500 mm, more preferably 5 to 300 mm.

The distance D2 is preferably 3000 mm or less because the height of a radiology room is usually approximately 3 m or less. The distance D2 is preferably 400 to 3000 mm, more preferably 500 to 2000 mm.

The distance (D1+D3) between the focus of the X-ray source 11 and the first grating 14 is preferably 300 to 3000 mm, more preferably 400 to 1800 mm.

The distance (D1+D3+D4) between the focus of the X-ray source 11 and the second grating 15 is preferably 400 to 3000 mm, more preferably 500 to 2000 mm.

These distances are the optimal distances for overlaying a grating image (self-image) from the first grating 14 on the second grating 15 and are calculated on the basis of the wavelength of the X-rays emitted from the X-ray source 11.

The X-ray source 11, the multislit grating 12, the object table 13, the first grating 14, the second grating 15, and the X-ray detector 16 are fixed to the support unit 17 and maintain their relative positions along the Z direction. The support unit 17 is an arm attached to the main unit 18 and can be moved in the Z direction with a driving unit 18A of the main unit 18.

The X-ray source 11 is attached to the support unit 17 with a cushioning 17A disposed therebetween. The cushioning 17A may be composed of any material that absorbs shock and vibration, such as an elastomer. Since the X-ray source 11 radiates heat during emission of X-rays, the cushioning 17A adjacent the X-ray source 11 is preferably composed of a heat insulating material.

The X-ray source 11 includes an X-ray tube, which generates X-rays propagating in the gravity direction (Z direction). The X-ray tube is, for example, a Coolidge X-ray tube or a rotary anode X-ray tube, which are commonly used in medical settings. The anode may be composed of tungsten or molybdenum.

The radius of the focus of the X-rays is preferably 0.03 to 3 mm, more preferably 0.1 to 1 mm.

A radiation field aperture (not shown) for restricting the X-ray irradiation area is disposed in the propagating path of the X-rays from the X-ray source 11.

Figure 2:
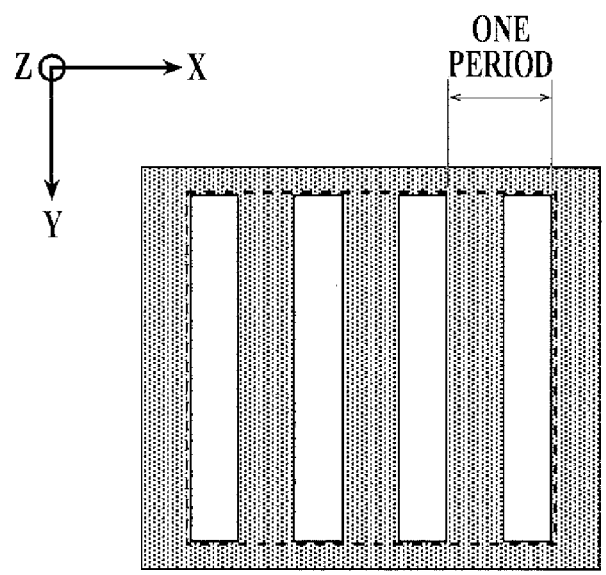
FIG. 2 is a plan view of a multislit grating.

A plurality of slits of the multislit grating 12 (third grating), which functions as a diffraction grating, are disposed at a predetermined pitch along the X direction, as illustrated in FIG. 2. The slit pattern of the multislit grating 12 is formed with a material having high X-ray blocking ability or high absorbance, such as tungsten, lead, or gold on a substrate composed of a material having low X-ray absorbance, such as silicon or glass. For example, a resist layer is covered with a mask having slits, and the mask is irradiated with ultraviolet (UV) rays to transfer the slit pattern to the resist layer, in a photolithographic process. The transferred slit pattern is exposed to form the slits in the resist layer. The slits are filled with metal through electroforming to form the multislit grating 12.

The period of the slits of the multislit grating 12 is 1 to 60 µm. The slit period corresponds to the distance between two adjacent slits, as shown in FIG. 2. The slit width (in the X direction) is typically 1% to 60%, preferably 10% to 40% of the slit period. The slit height (in the Z direction) is typically 1 to 500 µm, preferably 1 to 150 µm.

The slit period w0 (µm) of the multislit grating 12 is given by the following expression:

$$w0 = w1 \cdot (D3+D4)/D4$$

where w1 (µm) is the slit period of the first grating 14.

Selection of a period w0 satisfying the expression can make the self-images formed of X-rays passing through the multislit grating 12 and the slits in the first grating 14 overlap, and can focus them onto the second grating 15.

With reference to FIG. 1, a driver 12A that can move the multislit grating 12 in the X direction, which is orthogonal to the Z direction, is disposed adjacent to the multislit grating 12. The driver 12A has a single driving mechanism or a combination of multiple driving mechanisms having a relatively large reduction gear ratio, such as worm reducers.

The object table 13 is disposed at an object placing position in the X-ray propagating path from the X-ray source 11. An object is placed on the object table 13.

The first grating 14 is composed of a diffraction grating having multiple slits disposed at a predetermined period along the X direction, like the multislit grating 12 (see FIG. 2). Similar to the multislit grating 12, the slits of the first grating 14 may be formed through a photolithographic process with UV light. Alternatively, the first grating 14 may be composed of only a silicon substrate having fine deep lines on its surface formed by inductively coupled plasma (ICP) etching. The slit period of the first grating 14 is 1 to 20 µm. The slit width is typically 20% to 70%, preferably 35% to 60% of the slit period. The slit height is 1 to 100 µm.

If the first grating 14 is a phase grating, the slit height is set such that the phase difference is π/8 to 15×π/8 between the two materials that form the slit period, i.e., the materials of the X-ray transmissive portions and the X-ray blocking portions. Preferably, the slit height is set such that the phase difference is π/2 or π. If the first grating 14 is an absorption grating, the slit height is set such that the X-rays are sufficiently absorbed by the X-ray blocking portion.

If the first grating 14 is a phase grating, the distance D4 between the first grating 14 and the second grating 15 must substantially satisfy the following condition:

$$D4 = (m+1/2) \cdot w12/\lambda$$ i.

where m is an integer, and λ is the wavelength of the X-rays.

The second grating 15 is a diffraction grating having multiple slits disposed at a predetermined period along the X direction, like the multislit grating 12 (see FIG. 2). The second grating 15 can also be formed through a photolithographic process. The slit period of the second grating 15 is 1 to 20 µm. The slit width is typically 30% to 70%, preferably 35% to 60% of the slit period. The slit height is 1 to 100 µm.

The first grating 14 and the second grating 15 according to this embodiment each have a grating plane orthogonal to the Z direction (i.e., parallel to the XY plane). The slits in the first grating 14 are disposed on the XY plane at a slight angle from the slits of the second grating 15. Alternatively, the slits of the first grating 14 and second grating 15 may be parallel to each other.

The multislit grating 12, the first grating 14, and the second grating 15 have the following configurations:
the radius of the focus of the X-ray source 11: 300 µm;
the tube voltage: 40 kVp;
the thickness of the additional aluminum filter: 1.6 mm;
the distance D1 between the focus of the X-ray source 11 and the multislit grating 12: 240 mm;
the distance D3 between the multislit grating 12 and the first grating 14: 1110 mm;
the distance D3+D4 between the multislit grating 12 and the second grating 15: 1370 mm;
the size of the multislit grating 12: 10 mm2;
the slit period of the multislit grating 12: 22.8 µm;
the size of the first grating 14: 50 mm2;
the slit period of the first grating 14: 4.3 µm;
the size of the second grating 15: 50 mm2; and
the slit period of the second grating 15: 5.3 µm;

The region having the slits (for example, the region defined by the dotted lines in FIG. 2) in the multislit grating 12, the first grating 14, and the second grating 15 is referred to as "grating structure portion."

The X-ray detector 16 includes two-dimensionally arrayed transducers that generate electrical signals corresponding to the incident X-rays and detect these electrical signals as image signals.

The pixel size of the X-ray detector 16 is typically 10 to 300 µm, preferably 50 to 200 µm.

The X-ray detector 16 is preferably fixed to the support unit 17 and in contact with the second grating 15. This is because a large distance between the second grating 15 and the X-ray detector 16 causes blurring of the moire images acquired with the X-ray detector 16.

The X-ray detector 16 may be a flat panel detector (FPD). The FPDs usable in the invention are classified into indirect FPDs and direct FPDs. An indirect FPD converts the detected X-rays into electrical signals via photoelectric transducers, whereas a direct FPD directly converts the detected X-rays into electrical signals.

The indirect FPD has two-dimensionally arrayed pixels consisting of photoelectric transducers and thin-film transistors (TFTs) disposed below scintillator plates composed of, for example, CsI or GD2O2S. The X-rays incident on the X-ray detector 16 and absorbed in the scintillator plates cause the scintillator plates to emit light. The light charges the photoelectric transducers with electrons, which are detected as image signals.

The direct FPD includes an amorphous selenium film and electrodes deposited on a two-dimensional TFT array, the amorphous selenium film having a thickness of 100 to 1000 µm and being thermally deposited onto a glass plate. The X-rays absorbed in the amorphous selenium film generate electron-hole pairs in the film and causes an electrical potential difference, which is detected by the TFTs as voltage signals across the electrodes.

The X-ray detector 16 may alternatively comprise an imaging member, such as a charge coupled device (CCD) or an X-ray camera.

Figure 3:
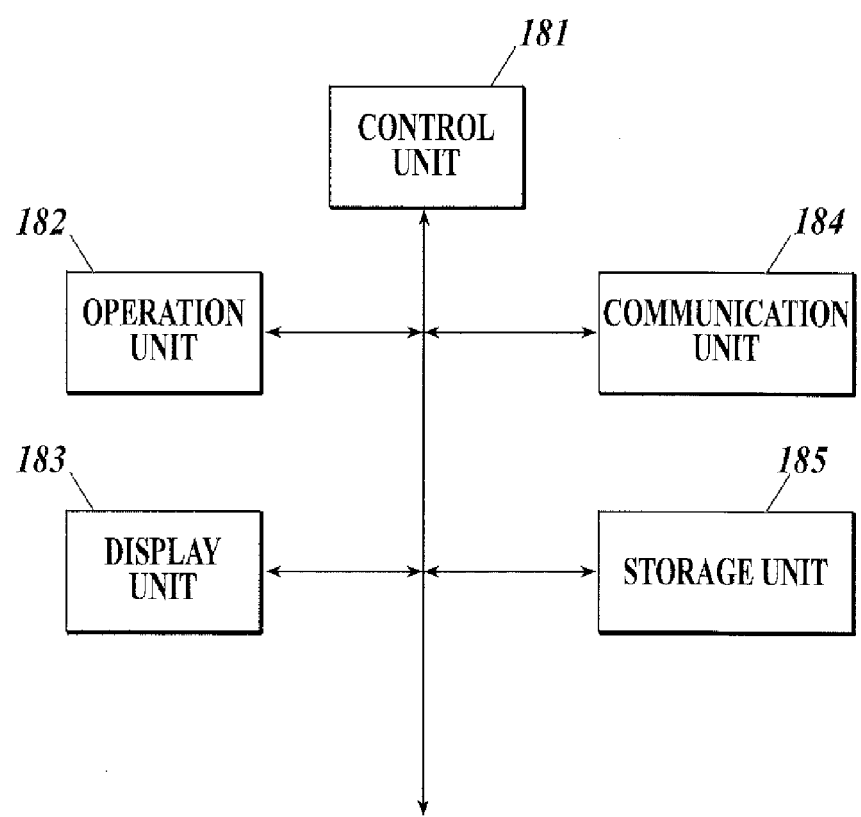
FIG. 3 is a block diagram illustrating the functional configuration of the main unit in FIG. 1.

With reference FIG. 3, the main unit 18 includes a control unit 181, an operating unit 182, a display 183, a communication unit 184, and a storage unit 185.

The control unit 181 includes a central processing unit (CPU) and a random access memory (RAM), and carries out a variety of processes in cooperation with the programs stored in the storage unit 185. The control unit 181 is connected to components, such as the X-ray source 11, the driver 12A, the driving unit 18A, and the X-ray detector 16. For example, the control unit 181 controls the timing and conditions of the X-ray emission from the X-ray source 11, the timing of the detection of the image signals by the X-ray detector 16, and the movement of the multislit grating 12 in accordance with the set information of imaging conditions input via the controller 5.

The operating unit 182 includes a radiation switch, which is operated to generate an operating signal to be sent to the control unit 181.

An operating menu and the operating state of the X-ray imaging apparatus 1 are displayed on a display 183 in accordance with the display control by the control unit 181.

The communication unit 184 includes a communication interface and communicates with the controller 5 in a network. For example, the communication unit 184 sends the moire stripe images read by the X-ray detector 16 and stored in the storage unit 185 to the controller 5.

The storage unit 185 stores programs to be executed by the control unit 181 and data required for the execution of the programs. The storage unit 185 stores moire stripe images acquired by the X-ray detector 16.

The controller 5 controls the imaging of the X-ray imaging apparatus 1 in response to operation by an operator. The controller 5 generates a reconstructed image of the object from a series of moire stripe images acquired in the X-ray imaging apparatus 1, post-processes the reconstructed image, and displays the processed image.

Figure 4:
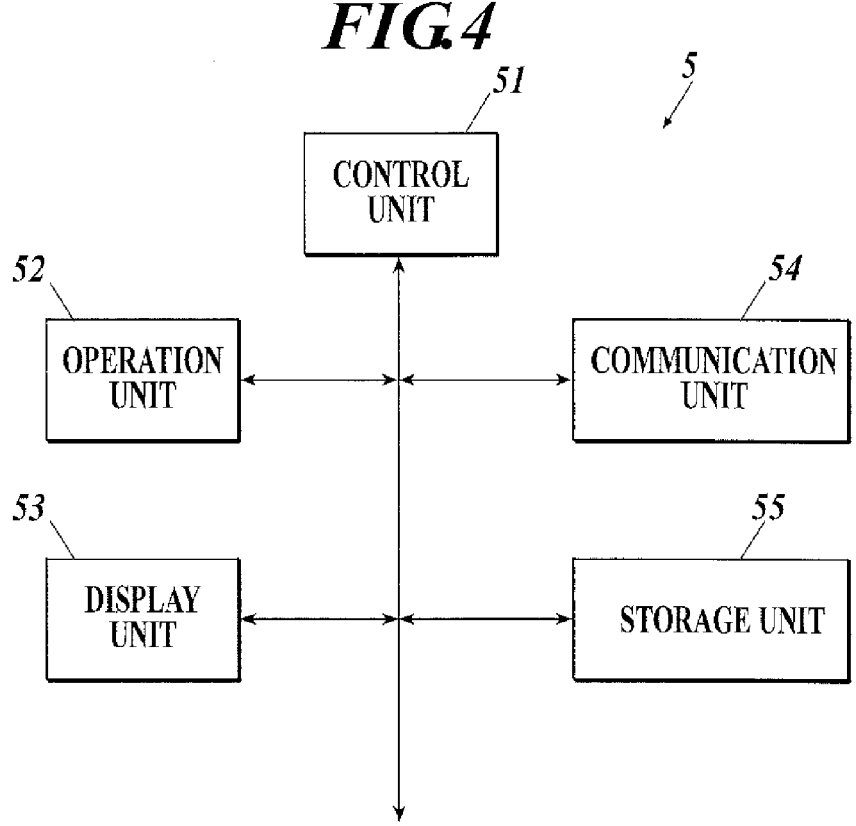
FIG. 4 is a block diagram illustrating the functional configuration of the control unit in FIG. 1.

With reference to FIG. 4, the controller 5 includes a control unit 51, an operating unit 52, a display 53, a communication unit 54, and a storage unit 55.

The control unit 51 includes a CPU and a RAM and carries out a variety of processes, such as the image generating/displaying process described below, in cooperation with the programs stored in the storage unit 55. The control unit 51 functions as a reconstruction-image generating member, a detecting member, a masked-image generating member, and an image processing member.

The operating unit 52 includes a keyboard having cursor keys, number keys, and function keys, and a pointing device, such as a mouse. The operating unit 52 sends operating signals corresponding to the operation of the keys on the keyboard and the operation of the mouse to the control unit 51. The display 53 has a touch panel integrated with a display. Operating signals corresponding to the operation of the touch panel and the display may be sent to the control unit 51.

The display 53 includes a monitor, such as a cathode ray tube (CRT) or a liquid crystal display (LCD), and displays images, such as an operating menu and reconstructed images, in accordance with the display control of the control unit 51.

The communication unit 54 includes a communication interface and establishes wire or wireless communication with the X-ray imaging apparatus 1 and X-ray detector 16 in a network. For example, the communication unit 54 sends the imaging conditions and control signals to the X-ray imaging apparatus 1 and receives moire stripe images from the X-ray imaging apparatus 1 and X-ray detector 16.

The storage unit 55 stores programs to be executed by the control unit 51 and data required for the execution of the programs. For example, the storage unit 55 stores imaging order information for programmed imaging by a radiology information system (RIS) or a hospital information system (HIS) (not shown). The imaging order information includes patient information, such as patient IDs and patient names, and information on the imaging site (object site).

The storage unit 55 stores imaging condition tables including the correspondence between the object sites and imaging conditions appropriate for the imaging site.

The storage unit 55 stores the imaging order information in correlation with moire stripe images acquired by the X-ray imaging apparatus 1 on the basis of the imaging order information and images reconstructed on the basis of the moire stripe images.

The storage unit 55 also previously stores information such as gain correction data and a defective pixel map for the X-ray detector 16. The defective pixel map includes position information (coordinates) of defective pixels (lost pixels) of the X-ray detector 16.

<Operation of X-ray Imaging System>

X-ray imaging with a Talbot-Lau interferometer of the X-ray imaging apparatus 1 will now be described.

Figure 5:
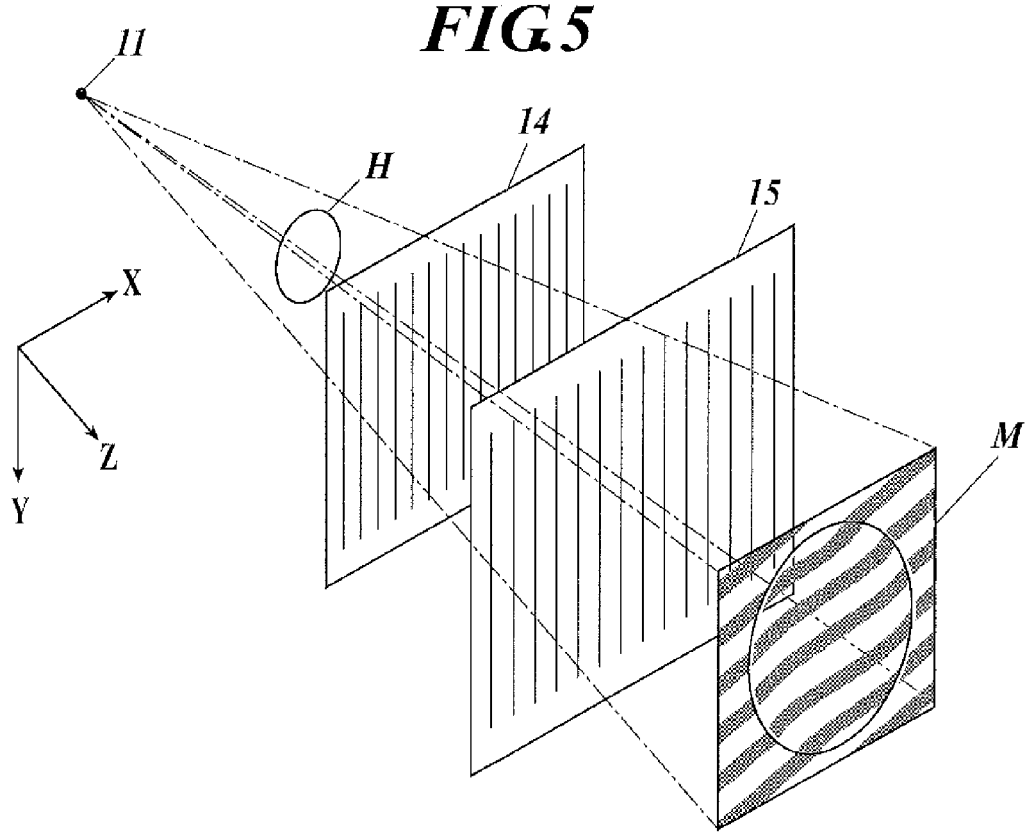
FIG. 5 illustrates the principle of a Talbot interferometer.

With reference to FIG. 5, X-rays emitted from the X-ray source 11 pass through the first grating 14 and form images at equal intervals along the Z direction. These images are known as "self-images." The formation of self-images is called the Talbot effect. The second grating 15 is disposed at a position where a self-image is formed and substantially parallel to the self-image. The X-rays passing through the second grating 15 form a moire stripe image (denoted by M in FIG. 5). Thus, the first grating 14 forms a periodic pattern, and the second grating 15 converts this periodic pattern into a moire stripe pattern. An object (denoted by H in FIG. 5) disposed between the X-ray source 11 and the first grating 14 causes a phase shift of the X-rays. Consequently, the moire stripe pattern of the moire stripe image are distorted near the contour of the object, as shown in FIG. 5. The moire stripe image can be processed to detect the distortion of the moire stripe pattern and form an image of the object. This is the principle of a Talbot interferometer.

The X-ray imaging apparatus 1 is provided with the multislit grating 12 disposed between the X-ray source 11 and the first grating 14 and closer to the X-ray source 11, and X-ray imaging is performed with the Talbot-Lau interferometer. An ideal Talbot interferometer has a point X-ray source, whereas the actual focus of the X-ray source 11 has a relatively large diameter. The X-rays from the X-ray source 11 passing through the multislit grating 12 appear as being emitted from multiple point sources. This is the principle of X-ray imaging with a Talbot-Lau interferometer, which achieves the same Talbot effect as a Talbot interferometer even with a relatively large focal diameter.

In the X-ray imaging system according to this embodiment, when imaging order information is selected through the operation of the operating unit 52 of the controller 5, imaging conditions corresponding to the object site assigned in the imaging order information are established in the X-ray imaging apparatus 1, and an imaging control process is carried out to acquire a radiographic image. The moire stripe images acquired through the radiographic process is sent to the controller 5, and a reconstructed image is generated based on these moire stripe images.

Figure 6:
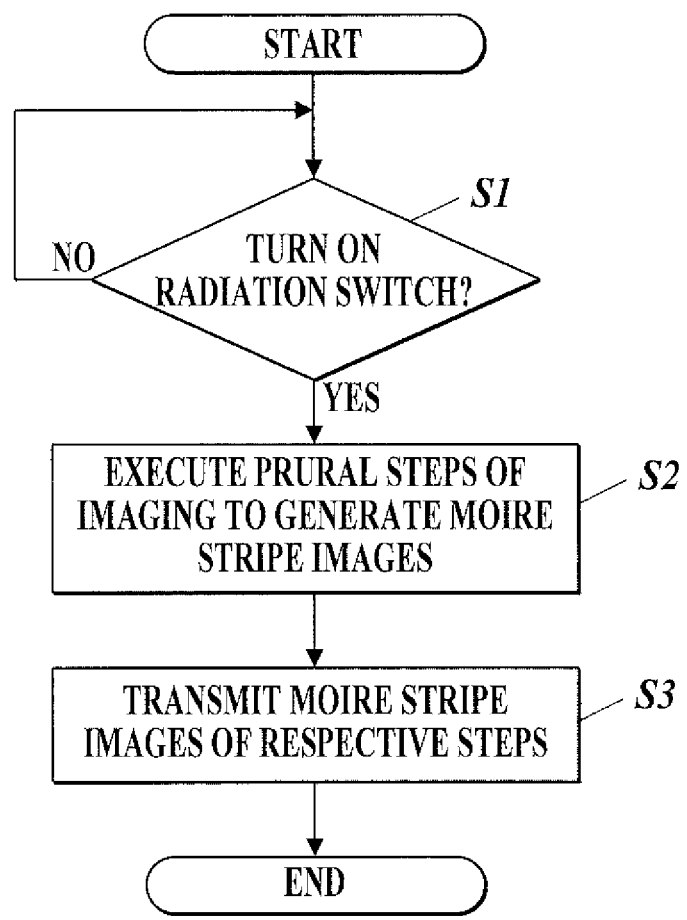
FIG. 6 is a flowchart illustrating the imaging control process carried out in the control unit in FIG. 3.

FIG. 6 is a flowchart illustrating the image control process carried out by the control unit 181 of the X-ray imaging apparatus 1. The imaging control process will now be described with reference to FIG. 6.

Upon operation of the radiation switch of the operating unit 182 by an operator (YES in Step S1), the control unit 181 controls the X-ray source 11, the X-ray detector 16, and the driver 12A to perform a series of imaging actions to acquire moire stripe images each of which has the moire stripe pattern of a different phase (Step S2).

The series of imaging actions begins with the emission of X-rays from the X-ray source 11 while the multislit grating 12 is in a stationary state. After resetting the X-ray detector 16 to remove unnecessary residual charges from the previous imaging process, recharging of the X-ray detector 16 begins upon emission of the X-rays. Upon stopping of the X-ray emission, the electrical charge is read as image signals. This is the first step in the series of imaging actions. Upon the end of the first step of imaging, the multislit grating 12 shifts by a predetermined distance, and the next step of imaging begins. Thus, the multislit grating 12 repeats movement and stop as many times as the number of steps of imaging. The X-rays are emitted and the image signals are read while the multislit grating 12 is in a stationary state. Upon completion of the imaging process carried out after the multislit grating 12 shifts for a total distance equal to one (1) slit period, the series of imaging actions is completed for multiple moire stripe images each of which has the moire stripe pattern of a different phase and is required for generating a single reconstructed image.

A series of imaging actions includes 2 to 20 steps, preferably 3 to 10 steps. The preferred number of steps is five for the acquisition of a highly visible reconstructed image within a short time (Reference document 1: K. Hibino, B. F. Oreb and D. I. Farrant, Phase shifting for Nonsinusoidal Wave Forms with Phase-shift Errors, J. Opt. Soc. Am. A., Vol. 12, 761-768(1995); and Reference document 2: A. Momose, W. Yashiro, Y. Takeda, Y. Suzuki and T. Hattori, Phase Tomography by X-ray Talbot Interferometetry for Biological Imaging, Jpn. J. Appl. Phys., Vol. 45, 5254-5262(2006)). A series of imaging actions having five steps will now be described.

Figure 7:
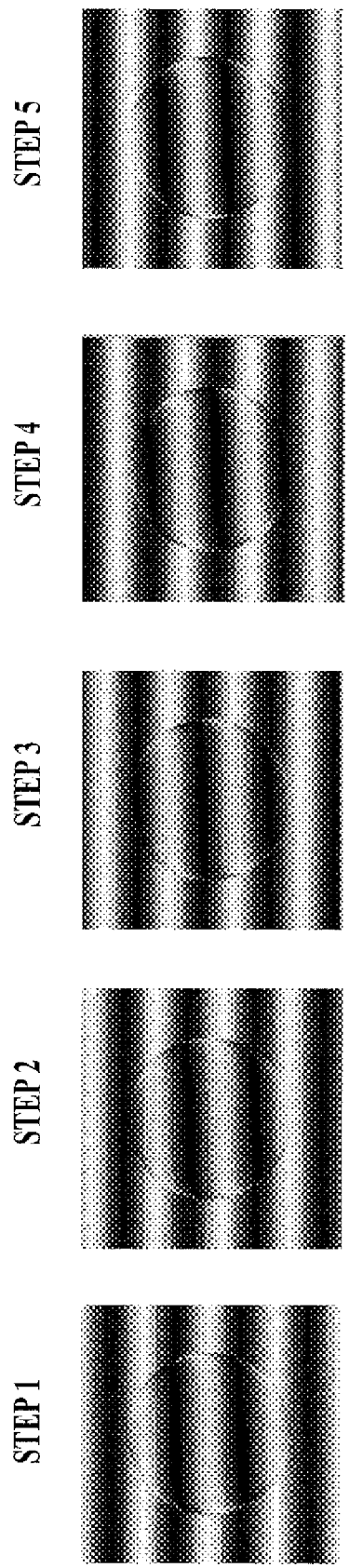
FIG. 7 is a moire stripe image acquired through five steps of imaging.

For example, the slit period of the multislit grating 12 is 22.8 µm, and the five steps of imaging are carried out in 10 seconds. An image is acquired every time the multislit grating 12 shifts by ⅕ of the slit period or 4.56 µm. In other words, an image is acquired at 2, 4, 6, 8, and 10 seconds after the radiation switch is turned on. If the multislit grating 12 is fed at a constant feeding rate with ideal precision, five moire stripe images corresponding to the shifting of the multislit grating 12 by a distance equal to one (1) slit period are acquired through the five steps of imaging, as illustrated in FIG. 7.

Upon completion of the series of imaging actions, the control unit 181 instructs the communication unit 184 to send these moire stripe images to the controller 5 (Step S3). The moire stripe images may be sent from the communication unit 184 to the controller 5 one at a time upon the completion of each step of imaging. Alternatively, all five moire stripe images may be sent upon completion of all steps of imaging.

According to this embodiment, X-ray imaging is carried out with an object placed on the object table 13 ("X-ray imaging with the object") and without the object placed on the object table 13 ("X-ray imaging without the object") to generate a series of moire stripe images each including the object in the X-ray imaging with the object and a series of moire stripe images each not including the object in the X-ray imaging without the object. The series of moire stripe images each including the object is referred to as "object moire stripe images," and the series of moire stripe images each not including the object is referred to as "BG moire stripe images."

Figure 8:
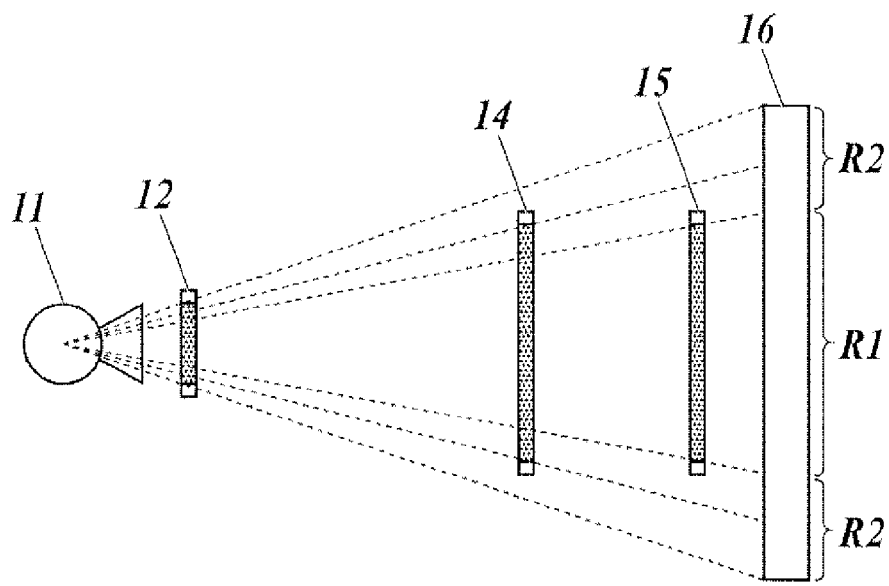
FIG. 8 illustrates in-grating regions and out-of-grating regions.

The regions of insufficient amounts of incident X-rays for the imaging of the object signals, such as a region outside the radiation field, in the object moire stripe images, the BG moire stripe images, and images generated from these moire stripe images (such as reconstructed images, phase images, and combined images) are referred to as "low-intensity X-ray regions." As illustrated in FIG. 8, the regions in these images on which X-rays are incident through the grating structure portions of all gratings, i.e., the multislit grating 12, the first grating 14, and the second grating 15, are referred to as "in-grating regions" (R1 in FIG. 8). The regions in the images other than the in-grating regions (regions on which X-rays are incident without passing through the grating structure portions of all gratings) are referred to as "out-of-grating regions" (R2 in FIG. 8). The dot-hatched regions in FIG. 8 represent the grating structure portions.

An insufficient amount of X-rays is incident on the radiation detector 16 in the low-intensity X-ray regions because the X-ray irradiation area is smaller than the detection area of the X-ray detector 16, a radiation field aperture is provided to restrict unnecessary X-rays, and/or part of the X-ray imaging apparatus intercepts the radiation field, blocking the X-rays.

Upon reception of the series of object moire stripe images and the series of BG moire stripe images from the main unit 18 by the communication unit 54 of the controller 5, the control unit 51 carries out an image generating/displaying process (image generating/displaying process A) to generate and display reconstructed images, such as a differential phase image and a small-angle scattering image, based on the received series of object moire stripe images and BG moire stripe images.

Figure 9:
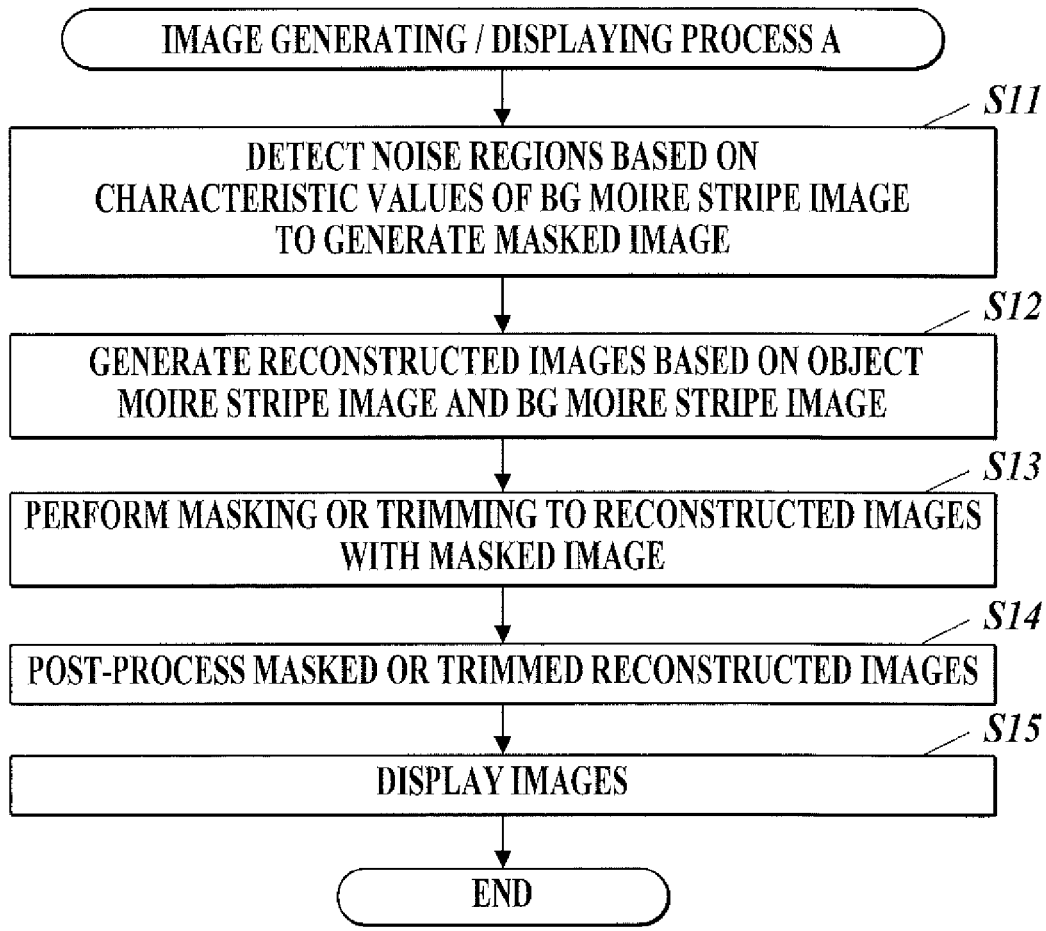
FIG. 9 is flowchart illustrating an image generating/displaying process A carried out by the control unit in FIG. 4 according to a first embodiment.

FIG. 9 is a flowchart illustrating the image generating/displaying process A carried out by the control unit 51 of the controller 5. The image generating/displaying process A is carried out by the control unit 51 in cooperation with the programs stored in the storage unit 55 in response to the operation of the operating unit 52.

The control unit 51 detects noise regions on the basis of the characteristic values of the BG moire stripe images received by the communication unit 54 and generates a masked image for identifying the detected noise regions (Step S11).

In the phase-contrast imaging with gratings, the moire stripe pattern is not formed in the low-intensity X-ray regions and the out-of-grating regions, and the differential phase image and the small-angle scattering image contain salt and pepper noise caused by a large variation in the pixel signal values resulting from the amplification of errors on photons and the X-ray detector 16 through computation (see FIGS. 21A and 21B). To generate a masked image for identifying the regions of salt and pepper noise in an image, the characteristic values of the BG moire stripe images are analyzed to detect noise regions in the low-intensity X-ray regions and the out-of-grating regions, which correspond to the salt and pepper noise regions in the differential phase image and the small-angle scattering image, in Step S11.

The noise in the low-intensity X-ray regions and the out-of-grating regions is inherent in the X-ray imaging system regardless of the object. Thus, this noise is referred to as "system noise."

The characteristic values of the moire stripe images will now be described. The characteristic values of the moire stripe images include average intensity (average intensity of the X-rays) a0, amplitude a1, phase Φ, visibility vis, and noise indices calculated from these parameters (which will be described below).

Figure 10:
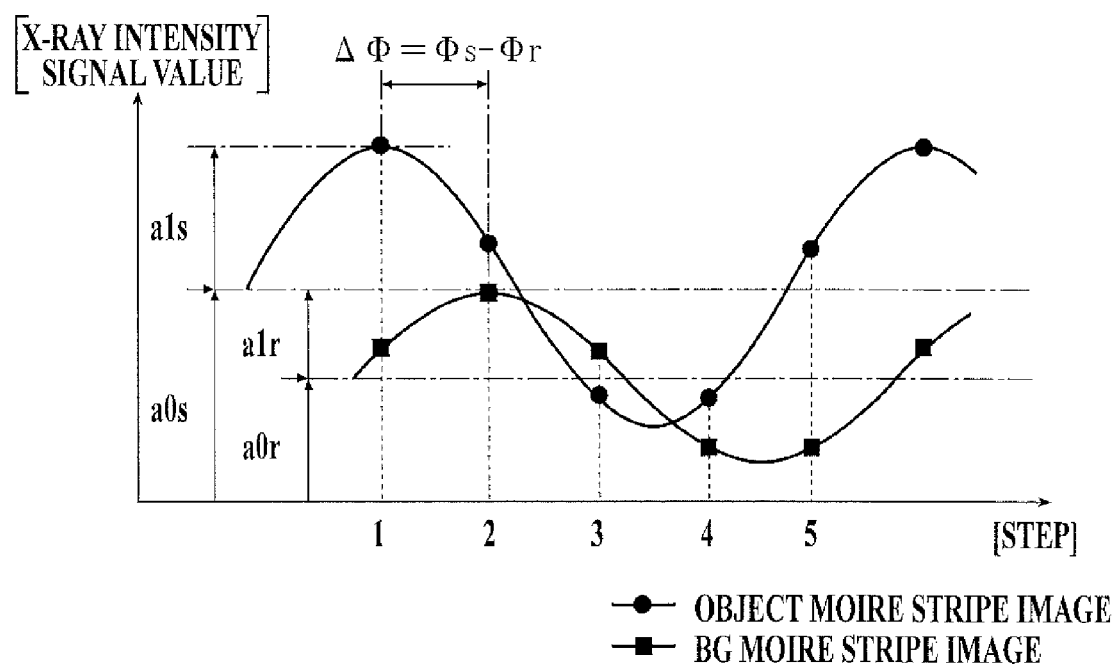
FIG. 10 illustrates the average intensity, amplitude, and phase of moire stripe images.

FIG. 10 is a graph illustrating example pixel signal values (X-ray intensity signal values) of any one pixel of moire stripe images acquired through the imaging control process described above. FIG. 10 is a graph illustrating the moire stripe images acquired in five imaging steps corresponding to one (1) slit period. With reference to FIG. 10, the pixel signal values representing the X-ray intensity of a single pixel in the moire stripe images varies in a substantially sinusoidal pattern. The sinusoidal pattern is defined by the following parameters: average intensity (average intensity of X-rays) a0, amplitude a1, and phase Φ. The subscript s is added to the parameters for the object moire stripe image, and the subscript r is added to the parameters for the BG moire stripe image, if the parameters need to be distinguished between those of the object moire stripe image and those of the BG moire stripe image, for example, in an expression or drawing. No subscripts are added to the parameters of the image as it is.

The average intensity a0(x, y), the amplitude a1(x, y), and the phase φ(x, y) for every pixel in a moire stripe image is given by Formulas 1 to 3, where I is the X-ray intensity signal value, "x, y" is the two-dimensional coordinates of the moire stripe image, and the M is the frequency of stripe scanning.

[Expression 1]

$$a_0(x, y) = \frac{\sum_{k=0}^{M-1} I_k(x, y)}{M} \quad \text{(Formula 1)}$$

[Expression 2]

$$a_1(x, y) = \frac{2\left|\sum_{k=0}^{M-1} I_k(x, y) \cdot \exp\left(-2\pi i \frac{k}{M}\right)\right|}{M} \quad \text{(Formula 2)}$$

[Expression 3]

$$\Phi(x, y) = \arg\left[\sum_{k=0}^{M-1} I_k(x, y) \exp\left(-2\pi i \frac{k}{M}\right)\right] \quad \text{(Formula 3)}$$

The visibility vis(x, y) for every pixel in the moire stripe image is given by Formula 4.

[Expression 4]

$$vis(x, y) = \frac{a_1(x, y)}{a_0(x, y)} = \frac{2\left|\sum_{k=0}^{M-1} I_k(x, y) \exp\left(-2\pi i \frac{k}{M}\right)\right|}{\sum_{k=1}^{M} I_k(x, y)} \quad \text{(Formula 4)}$$

A differential phase image is generated on the basis of the difference in the refractive indices of the object. The signal value DPh(x, y) for every pixel in the differential phase image is given by Formula 5 where Is(x, y) is the X-ray intensity signal value of the corresponding pixel in the object moire stripe image, Ir(x, y) is an X-ray intensity signal value of the corresponding pixel in the BG moire stripe image, Φs(x, y) is the phase of the corresponding pixel in the object moire stripe image, and Φr(x, y) is the phase of the corresponding pixel of the BG moire stripe image. Formula 5 defines the variation in the phase of the moire stripe pattern proportional to the difference in the refractive indices of the object and the tilt angle of the X-ray wave front, rather than the actual the difference in the refractive indices of the object and the tilt angle of the X-ray wave front. The variation in the phase of the moire stripe pattern is in the range of −0.5 to 0.5, and thus, the data signal of this value can be readily handled. Physical quantities of the object, such as the tilt angle of the X-ray wave front, can be defined by multiplying Formula 5 with $1/(2\pi\xi)$, where $\xi$ is a factor determined by the X-ray energy, the grating period, and/or the position of the object.

[Expression 5]

$$DPh(x, y) = \frac{1}{2\pi}[\Phi_s(x, y) - \Phi_r(x, y)] \quad \text{(Formula 5)}$$

$$= \frac{1}{2\pi} \arg\left[\frac{\sum_{k=0}^{M-1} Is_k(x, y) \exp\left(-2\pi i \frac{k}{M}\right)}{\sum_{k=0}^{M-1} Ir_k(x, y) \exp\left(-2\pi i \frac{k}{M}\right)}\right]$$

The signal value V(x, y) for every pixel of the small-angle scattering image is given by Formula 6, where Is(x, y) is the X-ray intensity signal value of the corresponding pixel in the object moire stripe image, Ir(x, y) is the X-ray intensity signal value of the corresponding pixel in the BG moire stripe image, viss(x, y) is the visibility of the corresponding pixel in the object moire stripe image, and visr(x, y) is the visibility of the corresponding pixel in the BG moire stripe image. Formula 6 defines the ratio of the visibility (visibility contrast), rather than the value proportional to the integral of the coefficient of scattering of the object in the irradiation direction of the X-rays. The ratio of the visibility is in the range of 0 to 1, and thus, the data signal of this value can be readily handled. A value proportional to the integral of the coefficient of scattering of the object can be defined by −ln(V(x, y)).

[Expression 6]

$$V(x, y) = \frac{vis_s(x, y)}{vis_r(x, y)} \quad \text{(Formula 6)}$$

$$= \frac{\sum_{k=0}^{M-1} Ir_k(x, y) \left|\sum_{k=0}^{M-1} Is_k(x, y) \exp\left(-2\pi i \frac{k}{M}\right)\right|}{\sum_{k=0}^{M-1} Is_k(x, y) \left|\sum_{k=0}^{M-1} Ir_k(x, y) \exp\left(-2\pi i \frac{k}{M}\right)\right|}$$

An absorption contrast image (hereinafter referred to as "absorption image") equivalent to a conventional X-ray absorption image can be derived from the same moire stripe images. The signal value T(x, y) for every pixel in the absorption image is given by Formula 7, where Is(x, y) is the X-ray intensity signal value of the corresponding pixel in the object moire stripe image, Ir(x, y) is the X-ray intensity signal value of the corresponding pixel in the BG moire stripe image, a0s(x, y) is the average intensity of the corresponding pixel in the object moire stripe image, and a0r(x, y) is the average intensity of the corresponding pixel in the BG moire stripe image. Formula 7 defines transmittance rather than the value proportional to the integral of the coefficient of absorption of the object in the irradiation direction of the X-rays. Transmittance is in the range of 0 to 1, and thus, the data signal of this value can be readily handled. A value proportional to the integral of absorbance of the object can be derived from $-\ln(T(x, y))$, if necessary.

[Expression 7]

$$T(x, y) = \frac{a_{0s}}{a_{0r}} = \frac{\sum_{k=0}^{M-1} Is_k(x, y)}{\sum_{k=0}^{M-1} Ir_k(x, y)} \quad \text{(Formula 7)}$$

Noise in the differential phase image and the small-angle scattering image will now be described.

The error $\sigma I(x, y)$ of the X-ray intensity signal value for every pixel in a moire stripe image due to photon noise of the X-rays is given by Formula 8, where $\sigma$ is the standard deviation, the over line represents average, I is the X-ray intensity signal value of the moire stripe image, and $\alpha$ is a coefficient that is associated with the sensitivity of the X-ray detector 16 (hereinafter referred to as "sensitivity coefficient") and converts the X-ray photons into detector signals. The sensitivity coefficient depends on the X-ray energy.

[Expression 8]

$$\sigma I(x, y)^2 = \alpha \overline{I(x, y)} \quad \text{(Formula 8)}$$

The phase error $\sigma\Phi(x, y)$ of the corresponding pixel in the moire stripe image due to the photon noise of the X-rays is given by Formula 9, based on law of propagation of error.

[Expression 9]

$$\sigma\Phi(x, y) = \frac{1}{\sqrt{2M}\pi}\sqrt{\frac{\alpha}{a_0(x, y)vis(x, y)^2}} \quad \text{(Formula 9)}$$

The relative error of visibility of the corresponding pixel in the moire stripe image due to the photon noise of the X-rays is given by Formula 10, also based on the law of propagation of error. The relative error of visibility is the quotient of the absolute error of visibility $\sigma vis(x, y)$ divided by the average visibility.

[Expression 10]

$$\frac{\sigma vis(x, y)}{vis(x, y)} = \sqrt{\frac{\alpha}{Ma_0(x, y)}\left(1 + \frac{2}{vis(x, y)^2}\right)} \quad \text{(Formula 10)}$$

Formulas 9 and 10 show that the phase error $\sigma\Phi(x, y)$ and the relative error of visibility increase as the average intensity $a_0(x, y)$ and/or the visibility $vis(x, y)$ decrease. Thus, if either the visibility $vis(x, y)$ or the average intensity $a_0(x, y)$ is small, the noise level is high. Since the visibility $vis(x, y)$ is the ratio of the amplitude $a_1(x, y)$ to the average intensity $a_0(x, y)$, the noise can be determined from the amplitude $a_1(x, y)$ and the average intensity $a_0(x, y)$.

The relative error of average intensity for every pixel in the moire stripe images is given by Formula 11, where $\sigma a_0(x, y)$ is the absolute error of average intensity. The relative error of average intensity is the quotient of the absolute error of average intensity divided by the average intensity.

[Expression 11]

$$\frac{\sigma a_0(x, y)}{a_0(x, y)} = \sqrt{\frac{\alpha}{Ma_0(x, y)}} \quad \text{(Formula 11)}$$

Based on these relational expressions, the relative error of visibility is defined as the root-mean-square of the phase error $\sigma\Phi(x, y)$ and the relative error of average intensity as given by Formula 12 and includes both the characteristics of the phase error $\sigma\Phi(x, y)$ and the relative error of average intensity. A pixel that generates intense noise at phase $\Phi(x, y)$ also generates intense noise at visibility $vis(x, y)$.

[Expression 12]

$$\left(\frac{\sigma vis(x, y)}{vis(x, y)}\right)^2 = \left(\frac{\sigma a_0(x, y)}{a_0(x, y)}\right)^2 + (2\pi \cdot \sigma\Phi(x, y))^2 \quad \text{(Formula 12)}$$

The relationship between the phase error $\sigma\Phi(x, y)$ and the relative error of average intensity is given by Formula 13.

[Expression 13]

$$(2\pi \cdot \sigma\Phi(x, y))^2 = \frac{2}{vis(x, y)^2}\left(\frac{\sigma a_0(x, y)}{a_0(x, y)}\right)^2 \quad \text{(Formula 13)}$$

The theoretical maximum value of the visibility is one (1). Actually, however, it is difficult to produce such an ideal grating and thus to enhance the coherence for X-rays. Thus, with the exception of special devices (systems), such as photon source facilities, the visibility $vis(x, y)$ is smaller than 1, and the empirically operational range is presumed to be approximately 0.1 to 0.7. If the visibility $vis(x, y)$ is 0.1 to 0.7, the influence of the phase error $\sigma\Phi(x, y)$ on the relative error of visibility is 4 to 200 times that of the relative error of average intensity. That is, the relative error of visibility is strongly influenced by the phase error $\sigma\Phi(x, y)$, and thus, the noise region due to phase and the noise region due to visibility can be treated as identical parameters, for simplicity.

The system noise regions in the differential phase image and the small-angle scattering image can be detected through the use of noise indices, such as the different errors described above. A noise index is used to evaluate the noise levels determined by the expressions for calculating the error in the moire stripe images and the error in the reconstructed images, as described below. Specifically, the noise levels includes values determined by the expressions for calculating the phase error, the relative and absolute errors of visibility, the relative and absolute errors of average intensity, the error of differential phase, the relative and absolute errors of small-angle scattering, and the relative and absolute errors of absorption; the simplified expressions without the sensitivity coefficient α (in which one (1) substitutes for α); and the expressions that are proportional to the expressions listed above.

[Detection of Noise Regions with Phase Noise Index of BG Moire Stripe Images]

A specific example of Step S11 in FIG. 9 will now be described through the processes of detecting a noise region with a phase noise index of every pixel in BG moire stripe images and generating a masked image, with reference to FIG. 11. The images in FIG. 11 are acquired through processing of actual BG moire stripe images.

The phase error σΦ(x, y) is given by Formula 9 for every pixel in the BG moire stripe images. This calculation requires the averages of a0(x, y) and vis(x, y). These averages can be determined with peripheral pixels. Although the averaging with the peripheral pixels makes the noise region to be detected ambiguous, such ambiguity is not a significant problem because the purpose of this process is to detect a region having a certain size, not defects in pixels. The averaging may lead to misdetection of pixels with noise as normal pixels and/or detection of minute defects in pixels inside the effective region of the images. Thus, after the generation of the masked image, it is preferred that isolated points or voids be removed or filled through contraction/expansion processing or the like. The sensitivity coefficient α of the X-ray detector 16 can be experimentally determined for each imaging condition as a parameter unique to the apparatus. Alternatively, a simplified noise index (α=1) may be used to avoid the use of actual α. The simplified noise index cannot determine the absolute value of noise, and thus, the simplified noise index should be treated as a relative index proportional to the noise.

After determining the phase error σΦ(x, y) for every pixel in the BG moire stripe images, pixels that have a phase error σΦ(x, y) larger than a predetermined threshold (referred to as "noise pixels") are detected, and a masked image is generated to identify the noise pixels. In a masked image, noise pixels and normal pixels have different assigned values, for example, "0" for noise pixels and "1" for other pixels (normal pixels), and thus are distinguishable from each other. In the masked image in FIG. 11, the black region indicates the noise region. The threshold that is a reference for detection may be a constant or may be a variable determined through an interclass variance in a histogram. A constant threshold may be set before shipment or during maintenance of the apparatus for every radiation condition (such as tube voltage, tube current, mAs value, and additional filter).

An example of the phase noise index has been described above. Alternatively, a visibility noise index may be used because the noise due to the phase and the noise due to the visibility have a correlation, and both noise indices can detect a substantially identical noise region. That is, a relative noise index for visibility may be used in place of the phase noise index. Alternatively, a noise index for absolute error (σvis) may be used in place of a relative noise index for visibility.

Figure 12A:
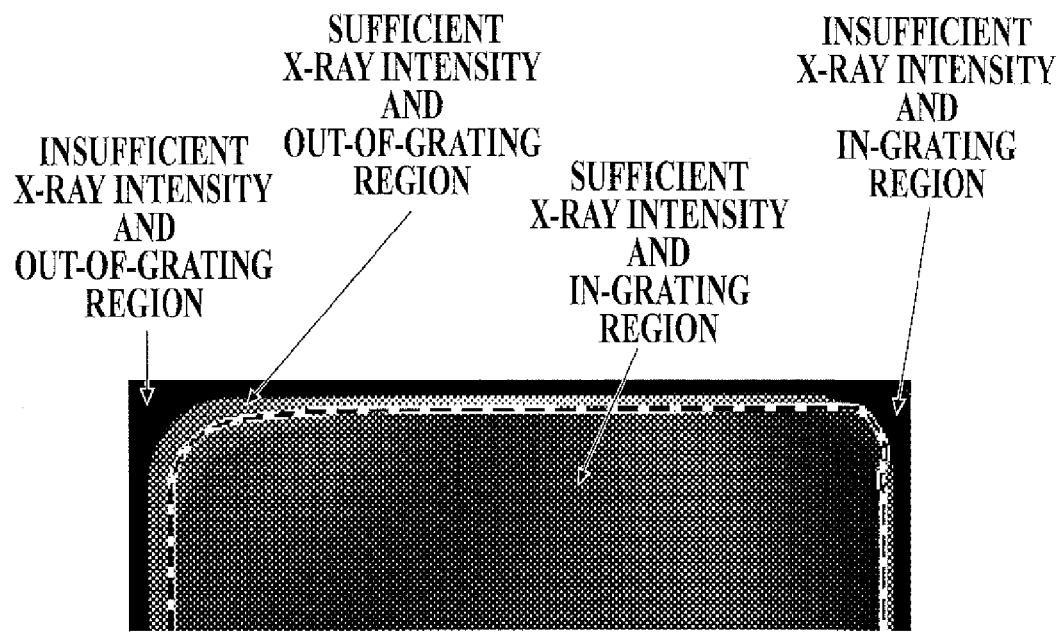
FIG. 12A illustrates noise regions detected in a BG moire stripe image.
Figure 12B:
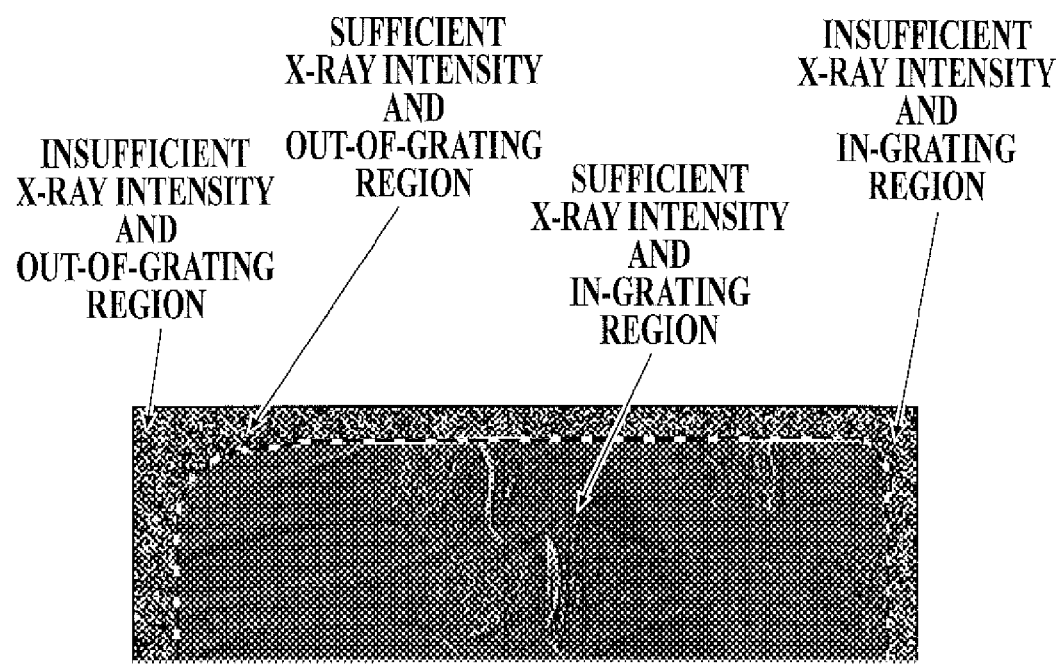
FIG. 12B illustrates salt and pepper noise regions in a differential phase image reconstructed based on the BG moire stripe image in FIG. 12A and an object moire stripe image.

FIGS. 12A and 12B illustrate the relationship between the noise region detected in a BG moire stripe image (see FIG. 12A) and a salt and pepper noise region in a differential phase image (see FIG. 12B) reconstructed based on the BG moire stripe image and an object moire stripe image. The dotted lines in FIGS. 12A and 12B represent the boundaries between the noise region detected in Step S11 and a noiseless region other than the noise region. With reference to FIGS. 12A and 12B, the noise region detected in Step S11 substantially coincides with the low-intensity X-ray region and/or the out-of-grating region in the BG moire stripe image. The noise region substantially coincides with the salt and pepper noise region in the differential phase image. Although not shown, such phenomena hold in the small-angle scattering image. The phenomena also hold in an object moire stripe image used in place of a BG moire stripe image. That is, the noise detection process in Step S11 according to the present invention detects salt and pepper noise regions in differential phase images and small-angle scattering images with high accuracy, and then can generate a masked image for masking these regions.

In the upper left region of the noiseless region (surrounded by the dotted line) in the BG moire stripe image illustrated in FIG. 12A, a region that appears as the out-of-grating region having sufficient X-ray intensity is actually an in-grating region. Although the in-grating region has an incomplete grating structure portion compared to the central portion and thus has low visibility, it is determined as an imaginable region in Step S11.

The process illustrated in the flowchart in FIG. 9 includes detecting noise regions for each imaging process and generating a masked image. For an apparatus having system noise regions without variation, it is preferred that the noise regions be detected before shipment or during maintenance, a masked image be generated, and the masked image be stored in the storage unit 55. If a masked image is prepared in advance, Step S11 can be skipped to reduce the processing time. If the system noise regions vary, the variation in the configuration of the noise regions (for example, the position of the radiation field aperture, and the relative positions of the gratings and the X-rays or the gratings and the X-ray detector 16) may be detected with a sensor so that the noise regions are redetected every time the variation occurs. Alternatively, the noise regions may be detected every time an image of an object is acquired (every time the calculation for a reconstructed image is carried out), as illustrated in FIG. 9.

For example, if a movable radiation field aperture is used, the low-intensity X-ray region may vary every time imaging is performed, and thus, the noise regions must be detected every time imaging is to be performed. The out-of-grating regions are substantially fixed to the apparatus. If the relative positions of the gratings and the X-rays or the gratings and the X-ray detector 16 vary due to replacement or degradation of parts, for example, the noise regions must be redetected.

[Detection of Noise Regions with Visibility and Average Intensity of BG Moire Stripe Images]

System noise is generated because an insufficient amount of X-rays is incident on the detector or the X-rays do not pass through the grating structure portions of all gratings. That is, the regions of system noise can be readily detected from the visibility vis and the average intensity a0 of the BG moire stripe images. The phase noise index or the visibility noise index is preferably used for accurate determination of the noise regions, but an alternative simple method can achieve satisfactory detection.

Figure 13:
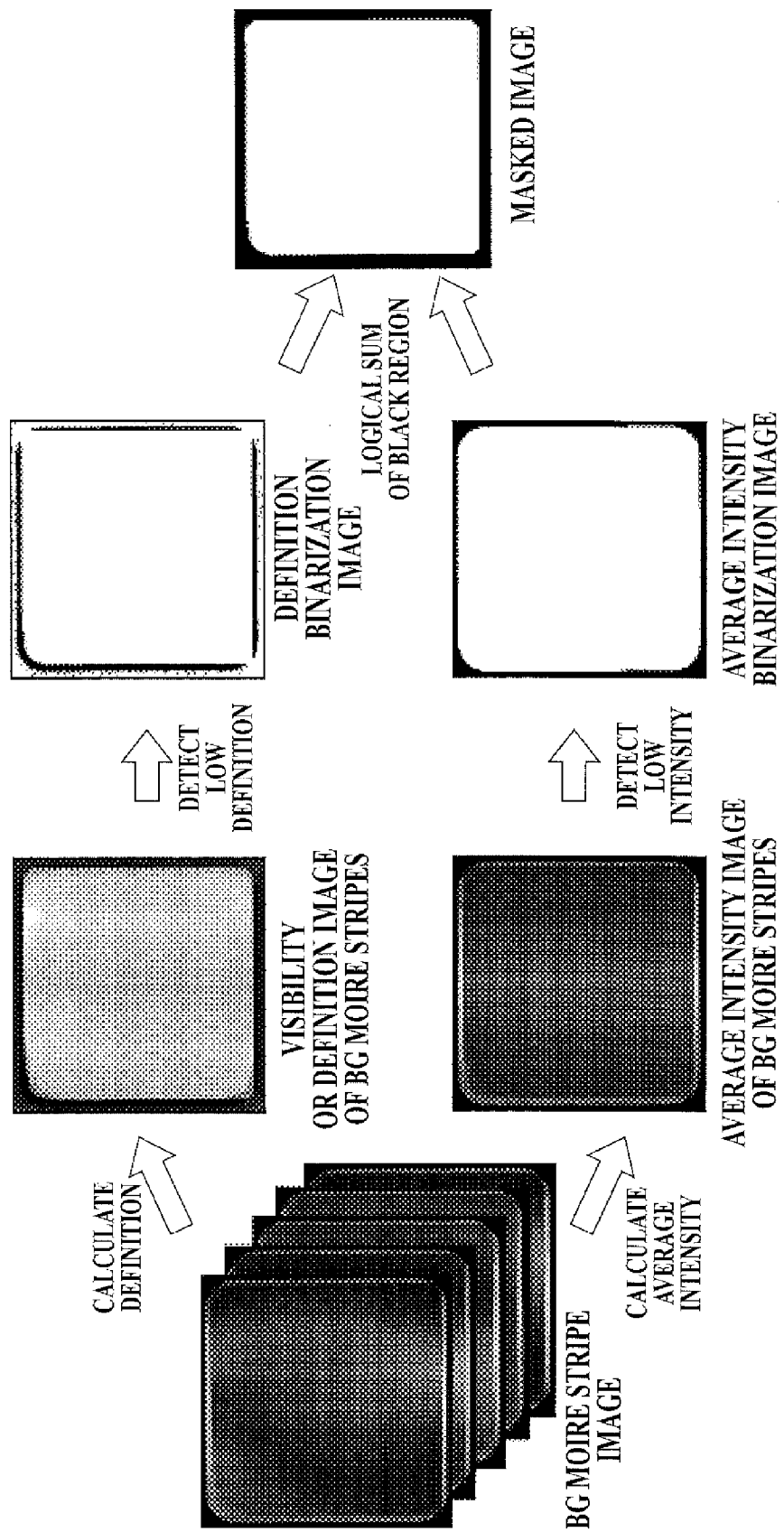
FIG. 13 illustrates the generating process of a masked image with noise indices for the visibility and average intensity of BG moire stripe images.

The detection of the noise regions with the visibility vis(x, y) and the average intensity a0(x, y) of the pixels in the BG moire stripe images and the generating process of a masked image will now be described with reference to FIG. 13. The images in FIG. 13 are acquired in the steps of the processing actually performed on the BG moire stripe images.

The visibility vis(x, y) is given by Formula 4 for every pixel in the BG moire stripe images. The determined visibility vis(x, y) is binarized with a predetermined threshold to detect the region of low visibility. The black region in the binarized image in FIG. 13 represents a low-visibility region of which the visibility is below the predetermined threshold.

The average intensity a0(x, y) is given by Formula 1 for every pixel in the BG moire stripe images. The determined average intensity a0(x, y) is binarized with a predetermined threshold to detect the region of low intensity. The black region in the binarized image in FIG. 13 represents a low-intensity region of which the average intensity is below the threshold.

The logical sum of the low-visibility region and the low-intensity region is obtained to detect the regions corresponding to the low-visibility region and/or the low-intensity region as noise regions. A masked image is then generated for the identification of the detected noise regions. The black region in the masked image in FIG. 13 is the noise regions.

the amplitude a1. The satisfactory detection of a system noise region with only the amplitude a1 of the BG moire stripe images was experimentally confirmed.

FIG. 14A illustrates a masked image generated from the phase error σΦ of the BG moire stripe pattern; FIG. 14B illustrates a masked image generated from the relative error of visibility; and FIG. 14C illustrates a masked image generated from only the amplitude a1. The masked images in FIGS. 14A to 14C are binarized with a constant threshold, and the isolated points or voids are removed or filled through contraction/expansion processing or the like. The black regions represent noise regions. Table 1 shows the binarization conditions used in FIGS. 14A to 14C and the number of pixels detected in noise regions. Identical system noise regions are detected through the three different detection schemes, as shown in the masked images in FIGS. 14A to 14C. The number of noise pixels in Table 1 differs depending on the detection scheme but only by several hundred pixels. This difference is more or less equivalent to one in every several tens of pixels displaced inward or outward from the boundary of the noise region. Consequently, rough detection of the noise region can be achieved with only the amplitude a1.

TABLE 1

|  | Detection of Noise Regions by Phase Error | Detection of Noise Regions by Definition Error | Detection of Noise Regions by Amplitude |
|---|---|---|---|
| Determination of Threshold and Noise Pixels | Pixel having a phase error at least six times larger than that of the pixels in the central area of the image are determined as noise pixels. | Pixel having a definition error at least six times larger than that of the pixels in the central area of the image are determined as noise pixels. | Pixel having an amplitude 1/6th or smaller of that of the pixels in the central area of the image are determined as noise pixels. |
| Number of Pixels Detected to Belong to Noise Regions | 282957 | 282745 | 282880 |
| Difference in Number of Noise Pixels Determined by Phase Error |  | −212 | −77 |

The setting of the threshold and the method of generating a masked image are the same as those for the phase noise index described above.

With reference to the masked images in FIGS. 11 and 13, the actual results of the simplified method based on the average intensity a0 and the visibility vis can detect substantially accurate noise regions, regardless of differences in detected pixels. The average intensity a0 and the visibility vis do not have to be acquired through additional calculation because they are already acquired through the calculation process of the differential phase image and the small-angle scattering image. Thus, the average intensity a0 and the visibility vis require less processing load than that of the calculation of the noise index. The average intensity a0 and the visibility vis varies due to photon noise, and thus, it is preferred that isolated points or voids in the masked image be removed or filled through contraction/expansion processing or the like.

[Detection of Noise Regions with Amplitude of BG Moire Stripe Images]

The system noise region is detectable with only the amplitude a1 of the BG moire stripe images.

Specifically, the differential phase noise and the small-angle scattering noise (refer to Formulas 14 and 15 described below) are associated with the amplitude a1 and the average intensity a0 but is more affected by the amplitude a1 than the average intensity a0; therefore, it is presumed that the noise region can be readily detected with only The amplitude a1 is already acquired through the calculation process of the differential phase image and the small-angle scattering image and thus does not recalculation. The noise detection with amplitude a1 has the fastest processing speed among the three detection schemes described above because only one parameter, i.e., amplitude a1, is used rather than two parameters, i.e., average intensity a0 and visibility vis. The method of detecting noise with amplitude a1 is suitable for a low-accuracy process that is frequently performed.

The specific steps of the process of detecting noise with the amplitude a1 involves calculation of the amplitude a1(x, y) of every pixel in the BG moire stripe images, binarization of the amplitude a1(x, y) with a predetermined threshold, and detection of the regions having an amplitude a1(x, y) smaller than the threshold. A masked image is generated for identifying the detected noise regions.

The setting of the threshold and the method of generating a masked image are the same as those for the phase noise index described above.

Referring back to FIG. 9, after generating process of a masked image, the control unit 51 generates three different types of reconstructed images, i.e., a differential phase image, a small-angle scattering image, and an absorption image, based on the object moire stripe image and the BG moire stripe image (Step S12).

The differential phase image is generated through calculation on every pixel in accordance with Formula 5. The small-angle scattering image is generated through calculation on every pixel in accordance with Formula 6. The absorption image is generated through calculation on every pixel in accordance with Formula 7. Three reconstructed images are generated in this embodiment. Alternatively, only the necessary reconstructed image(s), for example, selected by the user, may be generated.

The control unit 51 performs masking or trimming of the noise region with the masked image on the generated reconstructed image (Step S13).

The masking process replaces the signal values of the pixels in the noise regions with an identical value to hide the noise regions. The masking process involves multiplication of, for example, the signal values of the pixels in the differential phase image or the small-angle scattering image by the values of the corresponding pixels of the masked image. Alternatively, the masking process may involve assignment of a predetermined value for each image to the pixels determined to be noise pixels in the differential phase image and the small-angle scattering image. The predetermined value for each image is preferably a value that can be readily distinguished from the values of the object signal. For example, the predetermined value for the differential phase image is set to the maximum signal value +0.5, the minimum signal value −0.5, or the median value 0. The predetermined value for the small-angle scattering image is set to the maximum signal value 1, the minimum signal value 0, or the median value 0.5. Alternatively, the predetermined value may be set to a value not included in the effective range of the data, such as −1 or 2, to clearly distinguish the noise from the object signal.

FIGS. 15 and 16 illustrate example masking processes using identical masked images on the differential phase image and the small-angle scattering image. FIG. 15 illustrates the masking of the differential phase image, and FIG. 16 illustrates the masking of the small-angle scattering image. The noise regions are blacked out in the masking processes illustrated in FIGS. 15 and 16. Alternatively, the noise regions may be colored in other shades such as white or gray, or may be filled with other colors.

The moire stripe images may also be masked through the same process. A moire stripe image before acquiring a reconstructed image may be masked to avoid calculation for unnecessary pixels during the calculation for the reconstructed image. If a moire stripe image is stored in the storage unit 55, the trimming process described below may be performed on the moire stripe image to be stored to reduce the volume of data.

The absorption image derived from the same moire stripe image may be masked with an identical mask.

The masking process of the image may be replaced with the trimming of the image in order to reduce the noise region. FIG. 17 illustrates an example trimming process performed on the differential phase image. The trimmed region may be determined so as to include none of the noise pixels. Alternatively, the optimal size of the trimmed image may be determined on the basis of the size of the original image and noise pixels included in the original image, as shown in FIG. 17. For example, the size of an image can be calculated with an evaluation function derived from the size of the image and the number of noise pixels.

The optimal size of an image, for example, for a rectangular trimmed image, can be determined by setting xe, xs, ye and ys so that an evaluation function $f=(xe-xs)(ye-ys)-w*np^m$ (where $xs<xe$, $ys<ye$, $m>1$, and $w>0$) has a maximum value, where xs is the start point of the trimming in the transverse direction of the image, xe is the end point of the trimming in the transverse direction of the image, ys is the start point of the trimming in the longitudinal direction of the image, ye is the end point of the trimming in the longitudinal direction of the image, xe−xs is the number of trimmed pixels in the transverse direction of the image, ye−ys is the number of trimmed pixels in the longitudinal direction of the image, (xe−xs)*(ye−ys) is the number of pixels in the trimmed image, np is the number of pixels in the noise region, w is a weighting factor for the number of noise pixels, and m is the index for the number of noise pixels. The emphasis on either the size of the image or the number of noise pixels can be controlled by varying the weighting factor w and the index m. The evaluation function f described above includes the number of pixels in the noise region np. Alternatively, the sum or root-mean-square of the noise in the trimmed image may be determined with the noise index.

Referring back to FIG. 9, upon completion of the masking or trimming, the control unit 51 post-processes the masked or trimmed reconstructed image (Step S14).

Post-processing of the image, such as image correction, processing and combination, on the processed image subjected to masking or trimming can remove unnecessary noise regions from the image of interest. Therefore, the stability and speed of the post-processing performed on the processed image is enhanced more than post-processing performed on an unmasked image. Among various post-processing processes, correction on a differential phase image is disclosed in Japanese Patent Application Laid-Open No. 2012-170618, which describes the correction of non-uniform signals due to a variation in the relative positions of the gratings between image acquisitions for an object moire stripe image and a BG moire stripe image. Other processes include the generation of a phase image through integration of a differential phase image (refer to WO2012-029048); taking a difference between a differential phase image and a differential absorption image acquired through differentiation of an absorption image and subjected to weighting, or taking a difference between a phase image acquired through integration of a differential phase image and an absorption image subjected to weighting, to acquire an image from which bone and metal are eliminated (refer to WO2013-187150); and the combination of two or more reconstructed images (differential phase image, small-angle scattering image, and absorption image) (refer to Japanese Patent No. 5059107). Other processes include correction of beam hardening due to the gratings and the object, particle suppression, image sharpening, frequency processing, and gradation conversion, which are common image processing treatments.

Upon completion of the post-processing, the control unit 51 displays a post-processed image on the display 53 (Step S15) and ends the image generating/displaying process A.

<Second Embodiment>

A second embodiment of the present invention will now be described.

The detection process of system noise regions based on characteristic values of BG moire stripe images has been described in the first embodiment. The second embodiment describes an example detection process of system and object noise regions based on characteristic values of object moire stripe images.

The configuration of the X-ray imaging system and imaging control process according to the second embodiment are the same as those according to the first embodiment, and the redundant description thereof will not be repeated here.

During actual imaging of an object, the radiation exposure of the object may be reduced by applying an X-ray protective fabric over the object or narrowing the radiation field aperture to decrease the size of the radiation field to a size smaller than that for the imaging of BG moire stripe images. In such cases, salt and pepper noise occurs in regions of low X-ray intensity in the differential phase image and the small-angle scattering image, due to the protective fabric or the radiation field aperture. Such regions of salt and pepper noise cannot be estimated in the BG moire stripe images. Noise due to absorption and/or scattering by the object itself also cannot be detected in the BG moire stripe images. The noise due to absorption and/or scattering by the object, the noise due to an X-ray radiation field for the imaging of the object that is smaller than the X-ray radiation field for the imaging of BG moire stripe images, and the noise due to radiation reduction products, such as X-ray protective fabric, are inherent in the imaging of the object. Thus, these types of noise are referred to "object noise."

In the second embodiment, the characteristic values of object moire stripe images are used for the detection of noise regions. An object moire stripe image is formed on the X-ray detector 16 with X-rays that pass through the gratings (multislit grating 12, first grating 14, and second grating 15) and the object. An object moire stripe pattern is affected by system noise due to out-of-grating regions and low-intensity X-ray regions and object noise, and thus, regions of both system noise and object noise can be detected at once with the characteristic values of the object moire stripe pattern.

Figure 18:
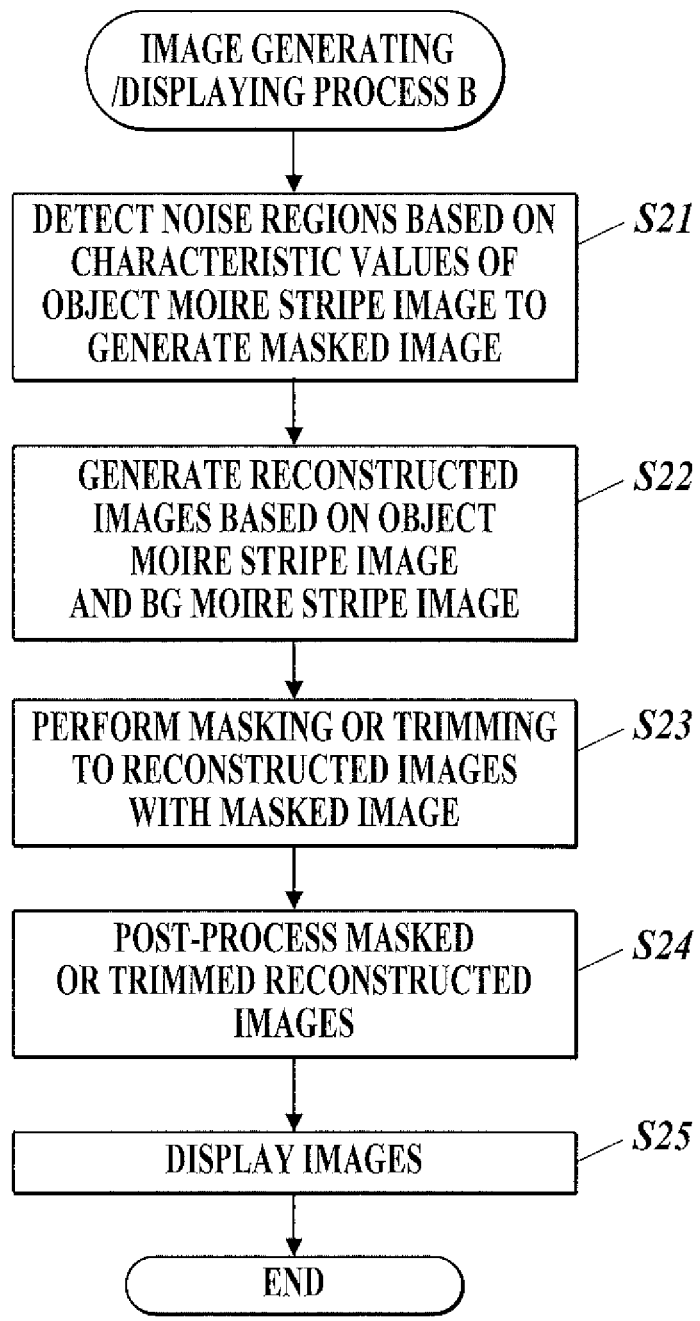
FIG. 18 is a flowchart illustrating an image generating/displaying process B performed in the control unit in FIG. 4 according to a second embodiment.

FIG. 18 is a flowchart illustrating an image generating/displaying process (image generating/displaying process B) carried out by the controller 5 according to the second embodiment. The image generating/displaying process B is carried out by the control unit 51 in cooperation with the programs stored in the storage unit 55 in response to the operation of the operating unit 52.

In the image generating/displaying process B, the control unit 51 detects noise regions on the basis of the characteristic values of the object moire stripe images received by the communication unit 54 and generates a masked image for identifying the detected noise regions (Step S21).

Step S21 is substantially the same as Step S11 in FIG. 9 for detecting noise regions in BG moire stripe images, and generating a masked image. That is, Steps S11 and S21 are the same except that object moire stripe images are used in place of BG moire stripe images. A characteristic value of an object moire stripe image may be a phase noise index or a visibility noise index. If a priority is given to processing speed over accuracy, the amplitude or a combination of average intensity and visibility may be used.

Since the object noise regions differ in every imaging process, the preferred detection timing of noise regions is during each imaging process of the object (each calculation process for a reconstructed image), as illustrated in the flowchart in FIG. 18.

After generating a masked image in Step S21, the control unit 51 carries out Steps S22 to S25. Steps S22 to S25 are the same as Steps S12 to S15 in FIG. 9 according to the first embodiment, and thus, the redundant description thereof will not be repeated here.

A method of separating a system noise region and an object noise region will now be described. The separation of system noise region and object noise region is difficult with only an object moire stripe image but can be achieved in combination with a BG moire stripe image. For example, after "0" is assigned to all pixels in the masked image for initialization, a system noise region A in the BG moire stripe image is detected, and "1" is assigned to the pixels in the masked image corresponding to the region A. A noise region B is detected in the object moire stripe image from the pixels not assigned by "1" in the masked image, and "2" is assigned to the pixels in the masked image corresponding to the region B. Since the region B does not contain the region A, the region B does not contain the system noise region and only contains the object noise region. The system noise region and the object noise region are identifiable in this way. The values assigned to the masked image are not limited to "1" and "2" and may be any other value.

A masked image generated from the characteristic values of the BG moire stripe image according to the first embodiment (hereinafter referred to as "masked image 1") and the masked image generated from the characteristic values of the object moire stripe image according to the second embodiment (hereinafter referred to as "masked image 2") may both be used for masking or trimming of a reconstructed image.

The noise detection with the characteristic values of the object moire stripe image can detect both system noise and object noise. If the system noise and the object noise are to be detected with thresholds of identical levels, the thresholds for determining noise are lowered to avoid the detection of object signals as false noise. Such lowered thresholds may cause the detection of system noise with low accuracy. To avoid this, for example, the level of the threshold for the generation of the masked image 1 may be set different from the level of the threshold for the generation of the masked image 2; the logical sum of the regions identified as noise in the masked images 1 and 2 may be determined to generate a masked image 3 from these regions in the masked image 1 and/or masked image 2; and the masked image 3 may be used for the masking or trimming of a reconstructed image. This achieves accurate detection of both the system noise and object noise.

<Third Embodiment>

A third embodiment of the present invention will now be described.

The third embodiment describes the calculation of a noise index for an image reconstructed on the basis of the characteristic values of the BG moire stripe images and the object moire stripe images and the detection of regions of system noise and object noise based on the noise index for the reconstructed image.

The configuration of an X-ray imaging system and imaging controlling process according to the third embodiment are identical to those according to the first embodiment, and thus, the redundant descriptions thereof will not be repeated here. An image generating/displaying process (image generating/displaying process C) according to the third embodiment will be described now.

FIG. 19 is a flowchart illustrating the image generating/displaying process C carried out by the controller 5 according to the third embodiment. The image generating/displaying process C is carried out by the control unit 51 in cooperation with the programs stored in the storage unit 55 in response to the operation of the operating unit 52.

The noise analysis of differential phase images and small-angle scattering images are disclosed in Reference document 3 (refer to Reference document 3: Vincent Revol, Rev. Sci. Instrum. 81 093709 (2010)).

The differential phase error $\sigma DPh(x, y)$ due to photon noise of the X-rays is given by Formula 14, based on the law of propagation of error, where $visr(x, y)$ is the visibility of a BG moire stripe image, $viss(x, y)$ is the visibility of an object moire stripe pattern, $a0r(x, y)$ is the average intensity of the BG moire stripe image, a0s(x, y) is the average intensity of the object moire stripe pattern, αr is the sensitivity coefficient of the detector during imaging of the BG moire stripe pattern, and αs is the sensitivity coefficient of the detector during imaging of the objective moire stripe pattern.

[Expression 14]

$$\sigma DPh(x, y) = \frac{1}{\sqrt{2M}\,\pi}\sqrt{\frac{\alpha_r}{a_{0r}(x,y)vis_r(x,y)^2} + \frac{\alpha_s}{a_{0s}(x,y)vis_s(x,y)^2}} \quad \text{(Formula 14)}$$

Similarly, the relative error of small-angle scattering is given by Formula 15, also based on the law of propagation of error, where σV(x, y) is the absolute error of small-angle scattering.

[Expression 15]

$$\frac{\sigma V(x,y)}{V(x,y)} = \sqrt{\frac{\alpha_r}{M a_{0r}(x,y)}\left(1 + \frac{2}{vis_r(x,y)^2}\right) + \frac{\alpha_s}{M a_{0s}(x,y)}\left(1 + \frac{2}{vis_s(x,y)^2}\right)} \quad \text{(Formula 15)}$$

The differential phase error σDPh, the relative error and absolute error of small-angle scattering, and the simplified and proportional expressions of these errors are referred to as the noise indices of a reconstructed image.

In the image generating/displaying process C, the control unit 51 calculates a differential phase noise indices on the basis of the BG moire stripe images and the object moire stripe images received from the communication unit 54, detects noise regions on the basis of the calculated noise indices, and generates a masked image M1 for identifying the detected noise regions (Step S31).

Specifically, the differential phase error σDPh(x, y) is given by Formula 14 for every pixel. This calculation requires the average of a0r(x, y) and a0s(x, y) and the average of visr(x, y) and viss(x, y). These averages can be determined with peripheral pixels. Although the averaging with the peripheral pixels makes the noise region to be detected ambiguous, such ambiguity is not a significant problem because the purpose of this process is to detect a region having a certain size, not defects in pixels. The averaging may lead to misdetection of pixels with noise as normal pixels and/or detection of minute defects in pixels inside the effective region of the images. Thus, after the generation of the masked image, it is preferred that isolated points or voids be removed or filled through contraction/expansion processing or the like. The sensitivity coefficient αr of the X-ray detector 16 during imaging of a BG moire stripe image can be experimentally determined for each imaging condition as a parameter unique to the apparatus.

The sensitivity coefficient αs for the imaging of an object moire stripe image varies depending on the X-ray curing of the object. If the imaging is limited to, for example, medical purposes, the sensitivity coefficient αs can be determined for every object and imaging condition, but if the imaging cannot be limited, the sensitivity coefficient αs is difficult to determine. In such a case, a simplified noise index (αr=αs=1) may be used without the sensitivity coefficient.

As described in Reference document 3, the sensitivity coefficient α varies depending on the object, but the variation is not significant in typical objects. Thus, a simplified noise index without α can be used to detect the general noise region. Since the absolute noise level cannot be determined with the simplified noise index, the simplified noise index must be treated as a relative index proportional to the noise.

The differential phase error σDPh(x, y) of every pixel is binarized with a predetermined threshold to detect pixels with intense noise (which are pixels having a differential phase error σDPh(x, y) greater than the predetermined threshold and referred to as "noise pixels"), and then a masked image M1 for identifying the noise pixels is generated. The setting of the threshold and the method of generating a masked image are the same as those for noise detection with the phase noise index described above.

The control unit 51 calculates the relative error (or absolute error) of small-angle scattering based on the BG moire stripe image and the object moire stripe image, detects the noise regions on the basis of the calculated relative error (or absolute error) of the small-angle scattering, and generates a masked image M2 (Step S32).

Specifically, the relative error (or absolute error) of the small-angle scattering for every pixel is given by Formula 15. The averaging of a0r(x, y) and a0s(x, y), the averaging of visr(x, y) and viss(x, y), and the calculation of the sensitivity coefficients αr and αs are the same for those in the noise detection with the differential phase σDPh(x, y). After the determination of the relative error (or absolute error) of the small-angle scattering, the noise index for the relative error (or absolute error) of the small-angle scattering for all pixels is binarized with a predetermined threshold to detect pixels with intense noise (which are pixels having a relative error (or absolute error) of the small-angle scattering greater than the threshold and referred to as "noise pixels"), and then a masked image M2 for identifying the noise pixels is generated.

The control unit 51 generates reconstructed images from the object moire stripe image and the BG moire stripe images (Step S33), and performs masking or trimming of the reconstructed images with the masked images M1 and M2 (Step S34).

Step S33 is the same as Step S12 in FIG. 9. In Step S34, the differential phase image is masked or trimmed with the masked image M1, and the small-angle scattering image is masked or trimmed with the masked image M2. Salt and pepper noise does not readily occur in absorption images. Thus, masking or trimming of an absorption image may not be performed, or otherwise may be performed with any one of the masked images described above. If pixels having a relative error of absorption greater than a predetermined threshold are detected with Formula 17, as described below, another masked image maybe used. Alternatively, as described in the first embodiment, the moire stripe images may be masked or trimmed with the masked images M1 and M2.

The process after Step S35 is the same as that after Step S14 in FIG. 9, and thus, the descriptions thereof will not be repeated here.

As described above in the image generating/displaying process C, a differential phase noise index and a small-angle scattering noise index may be calculated to generate two masked images. Alternatively, a single masked image may be generated from one of the noise indices and then applied to two images, for simplicity. The relative error of small-angle scattering is given by Formula 16 from the differential phase error σDPh(x, y) and the root-mean-square of the relative error of absorption. Formula 17 gives the relative error of absorption.

[Expression 16]

$$\left(\frac{\sigma V(x, y)}{V(x, y)}\right)^2 = \left(\frac{\sigma T(x, y)}{T(x, y)}\right)^2 + (2\pi \cdot \sigma DPh(x, y))^2 \quad \text{(Formula 16)}$$

[Expression 17]

$$\frac{\sigma T(x, y)}{T(x, y)} = \sqrt{\frac{\alpha_r}{M a_{0r}(x, y)} + \frac{\alpha_s}{M a_{0s}(x, y)}} \quad \text{(Formula 17)}$$

The relationship given by Formula 16 is the same as the relationship given by Formula 12 for the errors of visibility, phase, and average intensity in a moire stripe image. That is, the noise region of small-angle scattering and the noise region of differential phase can be treated as the same noise region, for simplicity, because the relative error of small-angle scattering is strongly influenced by the differential phase error. This means, a single masked image generated from either one of the noise indices may be applied to the two images, for simplicity. In such a case, the calculation for determining the other noise index is not required, and thus, processing time is reduced. Regardless of the use of either noise index, the masked image may contain isolated points and/or voids due to calculation errors. Thus, it is preferred to remove or fill these isolated points and/or voids through contraction/expansion processing.

The preferred timing for the detection of noise regions is during each imaging process of the object (each calculation process for a reconstructed image) because the object noise regions differ in every imaging process.

The system noise region and the object noise region can be distinguished for separation through the use of two masked images or, as described in the second embodiment, through the process of initializing the masked image, assigning "1" to the system noise region detected in the BG moire stripe images, and then assigning "2" to the object noise region detected with a noise index of a reconstructed image in pixels not included in the system noise region.

Similar to the combination of a masked image generated on the basis of the characteristic value of an object moire stripe image and a masked image generated on the basis of the characteristic value of a BG moire stripe image, the detection accuracy of system noise may be enhanced through masking or trimming with a masked image generated from the logical sum of a masked image M0 and a masked image M1, the masked image M0 being generated on the basis of the characteristic value of the BG moire stripe image according to the first embodiment with a threshold at a level different from that of the masked image M1. Similarly, the detection accuracy of system noise may be enhanced through masking or trimming with a masked image generated from the logical sum of a masked image M0 and a masked image M2, the masked image M0 being generated on the basis of the characteristic value of the BG moire stripe image.

<Fourth Embodiment>

A fourth embodiment of the present invention will now be described.

Figure 20A:
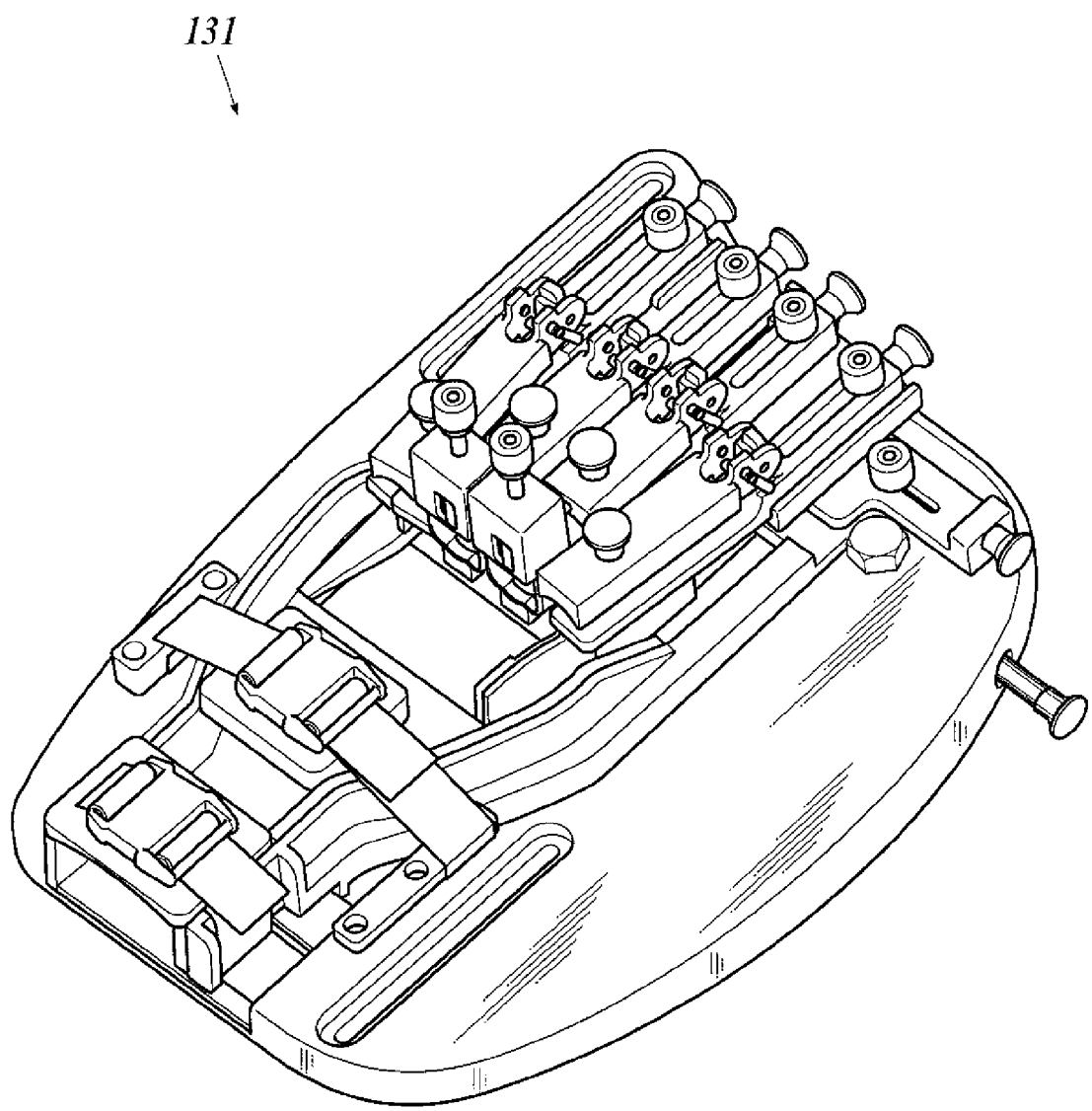
FIG. 20A illustrates an example imaging component.
Figure 20B:
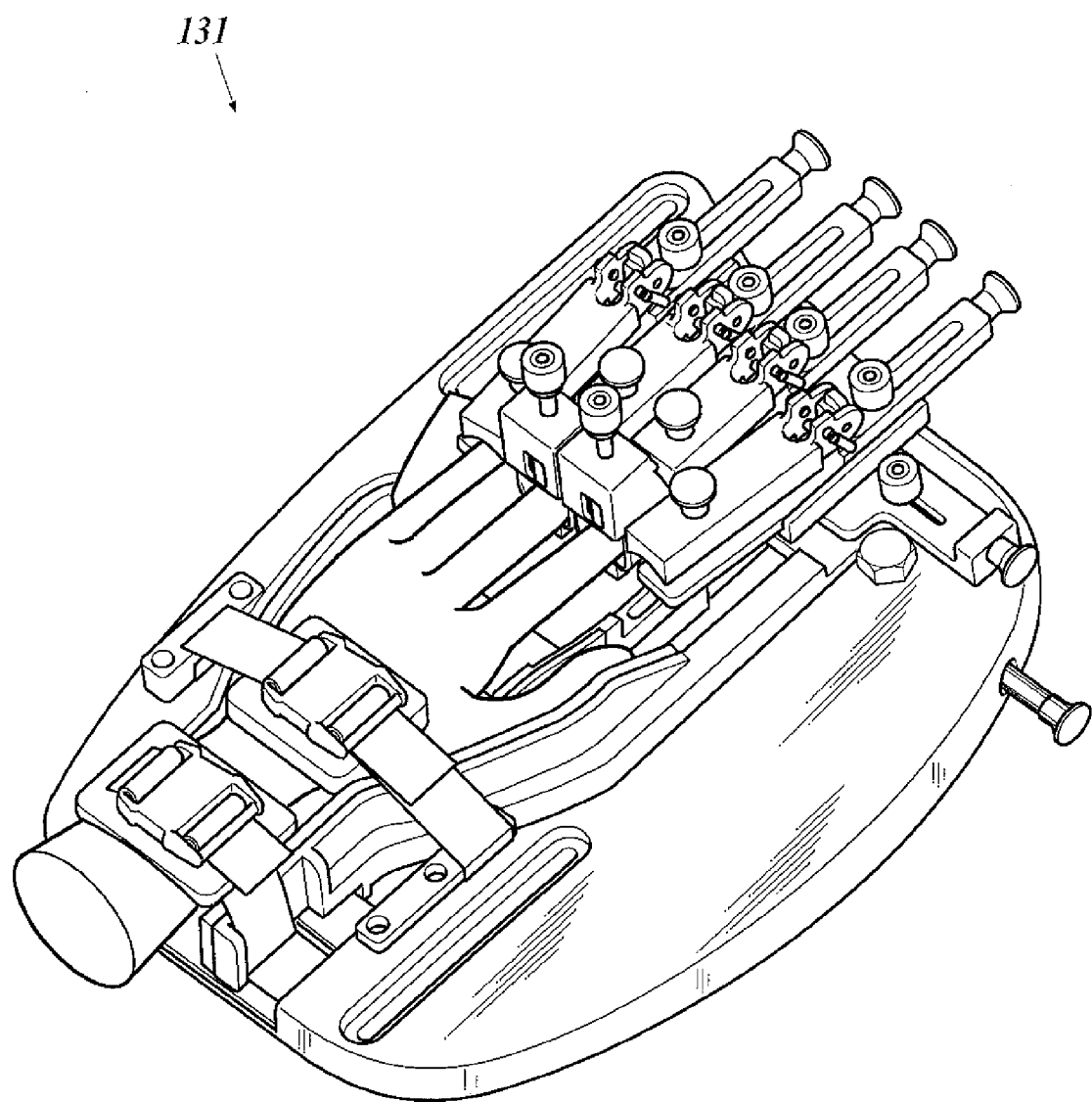
FIG. 20B illustrates an example imaging component attached to a hand and fingers.

The X-ray imaging system according the fourth embodiment includes a detachable imaging component 131 for securing an object to the object table 13 during imaging of the object. FIG. 20A illustrates an example imaging component 131. FIG. 20B illustrates the imaging component 131 in FIG. 20A that is attached to a hand and fingers, which are the object. The imaging component 131 should not be limited to a securing member (securing unit) that secures the object as illustrated in FIGS. 20A and 20B and may be a rotary table that rotates the object or a device that varies the state of the object (for example, a compressor, an expander, or a heater).

If the imaging component 131 holding the object intercepts the image during X-ray irradiation, the generated image will undesirably contain information unnecessary for diagnosis. The X-ray absorber and scatterer included the imaging component 131 impairs the stability of the processing, and the processing of unnecessary regions increases the processing time. Thus, it is desirable to detect the region corresponding to the imaging component 131 as a noise region through the noise detection according to the second or third embodiment (i.e., the detection of salt and pepper noise in a differential phase image and a small-angle scattering image) and mask or trim the detected region. Unfortunately, the imaging component 131 is often composed of partly metal and partly resin, which causes high and low portions on X-ray absorption and strong and weak portions on small-angle scattering. The small-angle scattering is the scattering in a small scattering angle region of X-rays in an object and lowers the visibility of a moire stripe image. In the noise detection according to the second or third embodiment, only the high absorbance portions, such as metal, or a small-angle scatterer is detected as a noise region, and the image still contains regions precluding the diagnosis. A larger region of the imaging component 131 can be detected as noise if the threshold for the noise region detection is lowered. This causes unintentional masking of the object signal region. If the noise level of the imaging component 131 and the object signal are the same, the region of the imaging component 131 cannot be readily separated from the object signal region with a mere threshold. If the imaging component 131 is known, the region of the imaging component 131 could be assigned as a noise region through an identification process based on parameters such as the shape and the level of X-ray absorption and scattering. Stable operation is difficult to achieve with a variation in the imaging conditions and positioning of multiple imaging components 131 and requires a complicated identification process.

To accurately detect the region of the imaging component 131 as a noise region through the noise detection according to the second or third embodiment, the entire imaging component 131 should have uniform and strong absorption or small-angle scattering features. The region of the imaging component 131 can be accurately and stably detected as a noise region through the application of an absorber that sufficiently absorbs X-rays or a small-angle scatterer that sufficiently scatters X-rays, for example, on the incident surface and/or the opposite surface, in the overlapping area of the region of the imaging component 131 and an object moire stripe image. If the noise levels of the signals from the object and the imaging component 131 are substantially the same, the object region might also be detected as a noise region. Thus, the absorber or small-angle scatterer applied to the imaging component 131 should preferably have absorbance or small-angle scattering higher than that of the object. In this way, the noise level of the object and the noise level of the absorber or small-angle scatterer will differ significantly. Thus, a variable threshold for noise detection can be stably determined through an interclass variance in a histogram. It is preferred that an absorber, if it is used, be disposed closer to the X-ray source 11 than the object to reduce unnecessary exposure of the object. The small-angle scatterer achieves the same effect on either the near or remote side of the object. Thus, the position of the small-angle scatterer can be determined on the basis of the conditions of the imaging component 131 and the apparatus. The absorber and the small-angle scatterer may be directly applied to the imaging component 131. Alternatively, they may be disposed apart from the imaging component 131 within the projection of the imaging component 131.

Alternatively, the absorber and the small-angle scatterer may be overlaid with part of the imaging component 131 on the object moire stripe image, and then the region of the imaging component 131 may be detected. For example, the absorber and small-angle scatterer may be disposed around the imaging component 131, and then the region surrounded by the absorber and small-angle scatterer may be detected as the region of the imaging component 131. Alternatively, the absorber and small-angle scatterer may be disposed at characteristic points defining the contour of the imaging component 131, and then the region defined by connecting these characteristic points may be detected as the region of the imaging component 131.

The absorber is preferably composed of gold, lead, tungsten, iron, aluminum, copper, platinum, or iridium, but may be composed of any other material that sufficiently absorbs X-rays. The materials suitable for the small-angle scatterer include fine powder, liquid and resin which contain air bubbles, paper, and wood. The bubbles may be replaced with metal or resin microspheres. The preferred particle size of the powder, bubbles, or microspheres is approximately half the grating period of the first grating. The absorber and the small-angle scatterer may be combined.

As described above, the control unit 51 of the controller 5 in the X-ray imaging system detects a salt and pepper noise region in a differential phase image and a small-angle scattering image on the basis of the characteristic values of at least one of the moire stripe images each including the object and the moire stripe images each not including the object received from the X-ray imaging apparatus 1, and generates a masked image for identifying the detected salt and pepper noise region. At least one of a reconstructed image and the moire stripe images is masked or trimmed with the generated masked image.

This provides readily diagnosable and examinable differential phase images and small-angle scattering images without salt and pepper noise regions that are indistinguishable from the object region. The removal of unnecessary salt and pepper noise regions that do not contain objected signals enhances the stability and speed of the post-processing.

For example, the control unit 51 can calculate a phase noise index or a visibility noise index for moire stripe images each not including the object and detect salt and pepper noise regions in the differential phase image and the small-angle scattering image on the basis of the calculated noise index.

The control unit 51 can calculate the visibility and the average intensity of the moire stripe images each not including the object and detect salt and pepper noise regions in the differential phase image and the small-angle scattering image on the basis of the calculated visibility and average intensity.

The control unit 51 can calculate the amplitude of the moire stripe images each not including the object and detect salt and pepper noise regions in the differential phase image and the small-angle scattering image on the basis of the calculated amplitude.

The control unit 51 can calculate the phase noise index or the visibility noise index of the moire stripe images each including the object and detect salt and pepper noise regions in the differential phase image and the small-angle scattering image on the basis of the calculated noise index.

The control unit 51 can calculate the visibility and the average intensity of the moire stripe images each including the object and detect salt and pepper noise regions in the differential phase image and the small-angle scattering image on the basis of the calculated visibility and average intensity.

The control unit 51 can calculate the amplitude of the moire stripe images each including the object and detect salt and pepper noise regions in the differential phase image and the small-angle scattering image on the basis of the calculated amplitude.

The control unit 51 can calculate the differential phase noise index or the small-angle scattering noise index on the basis of the moire stripe images each including the object and the moire stripe images each not including the object and detect salt and pepper noise regions in the differential phase image and the small-angle scattering image on the basis of the differential phase noise index or the small-angle scattering noise index.

By disposing an X-ray absorber or X-ray small-angle scatterer in the overlapping area of the region of the imaging component 131 and an object moire stripe image, the region of the imaging component 131 that should not be included in the image can be detected as a salt and pepper noise region.

The embodiments described above are mere examples, and the present invention should not be limited to these embodiments.

In the embodiments described above, the X-ray imaging apparatus includes a Talbot-Lau interferometer that involves shift of the multislit grating 12 with respect to the first grating 14 and the second grating 15 during an imaging process. Alternatively, the X-ray imaging apparatus according to the present invention may include a Talbot-Lau interferometer that involves shift of one or two of the multislit grating 12, the first grating 14, and the second grating 15. Another X-ray imaging apparatus according to the present invention may include a Talbot interferometer that involves shift of the first grating 14 or the second grating 15 with respect to the other grating.

Alternative to the stripe scanning according to the embodiments, any other method of calculating a phase contrast image may be applied. For example, a phase contrast image can be acquired from a single object moire stripe image and BG moire stripe image through methods such as the Fourier-Transform Method described in Reference document 4 (refer to Reference document 4: M. Takeda, H. Ina, and S. Kobayashi, "Fourier-Transform Method of Fringe-Pattern Analysis for Computer-Based Topography and Interferometry," J. Opt. Soc. Am. 72, 156 (1982)) and the method disclosed in Japanese Patent Application Laid-Open No. 2012-143491. Other methods include diffraction enhanced imaging (DEI) without grating. Regardless of the method employed, noise regions are detectable through the process according to the present invention because amplitude, phase, and average intensity can be obtained through the calculation process of acquiring a phase contrast image. That is, the present invention should not be limited to stripe scanning.

In the embodiments described above, the X-ray imaging system comprises a multislit grating 12, a first grating 14, and a second grating 15 that are one-dimensional gratings. Alternatively, the X-ray imaging system according to the present invention may perform two-dimensional stripe scanning with two-dimensional gratings.

In the embodiments described above, three different types of reconstructed images are generated. Alternatively, the X-ray imaging system according to the present invention may generate at least one of the differential phase image and the small-angle scattering image.

The detailed configurations and operation of the components of the X-ray imaging system may be appropriately modified without departing from the scope of the invention.

Japanese Patent Application No. 2014-026087 filed on Feb. 14, 2014 is hereby incorporated by reference in its entirety.

What is claimed is:

1. An X-ray imaging system comprising:
    an X-ray source which emits an X-ray;
    a first grating having a periodic pattern and disposed in an X-ray propagating path;
    a second grating which converts the periodic pattern of the first grating into a moire stripe pattern;
    an X-ray detector including two-dimensionally arrayed transducers which generate an electrical signal corresponding to the incident X-ray emitted from the X-ray source and passing through the first grating and the second grating, the X-ray detector reading the electrical signal generated by the transducers as an image signal to acquire a moire stripe image;
    a reconstructed image generating member which generates at least one reconstructed image of a differential phase image and a small-angle scattering image of an object based on one or more moire stripe images not including the object and one or more moire stripe images including the object, the moire stripe image not including the object being acquired through irradiation of an object position without the object in the X-ray propagating path with the X-ray from the X-ray source, the moire stripe image including the object being acquired through irradiation of the object at the object position with the X-ray from the X-ray source;
    a detecting member which detects a salt and pepper noise region in the reconstructed image based on at least one of differential phase noise index, small-angle scattering noise index, phase noise index and visibility noise index calculated by one or more moire stripe images not including the object, and/or one or more moire stripe images including the object;
    a masked-image generating member which generates a masked image for identifying the detected salt and pepper noise region; and
    an image processing member which masks or trims at least one of the reconstructed image and the moire stripe images with the generated masked image.

2. The X-ray imaging system of claim 1, further comprising an X-ray absorber overlaid with an imaging component on the moire stripe image including the object, the imaging component being used during irradiation of the object at the object position with the X-ray.

3. The X-ray imaging system of claim 1, further comprising an X-ray small-angle scatterer overlaid with an imaging component on the moire stripe image including the object, the imaging component being used during irradiation of the object at the object position with the X-ray.

4. The X-ray imaging system of claim 1, further comprising a third grating disposed between the X-ray source and the first grating.

5. A method of processing an image in an X-ray imaging system comprising:
    an X-ray source which emits an X-ray;
    a first grating having a periodic pattern and disposed in an X-ray propagating path;
    a second grating which converts the periodic pattern of the first grating into a moire stripe pattern;
    an X-ray detector including two-dimensionally arrayed transducers which generate an electrical signal corresponding to the incident X-ray emitted from the X-ray source and passing through the first grating and the second grating, the X-ray detector reading the electrical signal generated by the transducers as an image signal to acquire a moire stripe image; and
    a reconstructed image generating member which generates at least one reconstructed image of a differential phase image and a small-angle scattering image of an object based on one or more moire stripe images not including the object and one or more moire stripe images including the object, the moire stripe image not including the object being acquired through irradiation of an object position without the object in the X-ray propagating path with the X-ray from the X-ray source, the moire stripe image including the object being acquired through irradiation of the object at the object position with the X-ray from the X-ray source;
    the method comprising the:
    detecting a salt and pepper noise region in the reconstructed image based on at least one of differential phrase noise index, small-angle scattering noise index, phrase noise index and visibility noise index calculated by one or more moire stripe images not including the object and/or one or more moire stripe images;
    generating a masked image for identifying the detected salt and pepper noise region; and
    masking or trimming at least one of the reconstructed image and the moire stripe images with the generated masked image.

* * * * *